United States Patent
Peti et al.

(10) Patent No.: US 9,453,061 B2
(45) Date of Patent: Sep. 27, 2016

(54) METHOD AND COMPOSITIONS FOR TREATMENT OF CALCINEURIN-RELATED DISEASES

(71) Applicant: BROWN UNIVERSITY, Providence, RI (US)

(72) Inventors: Wolfgang Peti, Barrington, RI (US); Rebecca Page, Barrington, RI (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

(21) Appl. No.: 14/819,623

(22) Filed: Aug. 6, 2015

(65) Prior Publication Data

US 2016/0038571 A1    Feb. 11, 2016

Related U.S. Application Data

(60) Provisional application No. 62/033,766, filed on Aug. 6, 2014.

(51) Int. Cl.
| | |
|---|---|
| *A61K 38/17* | (2006.01) |
| *C07K 14/47* | (2006.01) |
| *C12N 9/16* | (2006.01) |
| *A61K 33/06* | (2006.01) |

(52) U.S. Cl.
CPC .......... *C07K 14/4703* (2013.01); *A61K 33/06* (2013.01); *A61K 38/1738* (2013.01); *C12N 9/16* (2013.01); *C07K 2319/23* (2013.01); *C07K 2319/24* (2013.01)

(58) Field of Classification Search
None
See application file for complete search history.

(56) References Cited

PUBLICATIONS

Chan, Betty et al, "Identification of a peptide fragment of DSCR1 that competitively inhibits calcineurin activity in vitro and in vivo." PNAS (2005) 102(37) p. 13075-13080.*
Yampolsky, Lev Y. and Stoltzfus, Arlin, "The exchangeability of amino acids in proteins." Genetics (2005) 170 p. 1459-1472.*
Olsen, J. V. et al. Quantitative phosphoproteomics reveals widespread full phosphorylation site occupancy during mitosis. Sci Signal 3(104):ra3 (2010).
Panigrahi, K. et al. The alpha,alpha-difluorinated phosphonate L-pSer-analogue: an accessible chemical tool for studying kinase-dependent signal transduction. Chem Biol 16, 928-36 (2009).
Peti, W. et al. Strategies to make protein serine/threonine (PP1, calcineurin) and tyrosine phosphatases (PTP1B) druggable: achieving specificity by targeting substrate and regulatory protein interaction sites. Bioorganic and Medicinal Chemistry, 23: 2781-2785 (2015).
Peti, W. et al. Structural basis for protein phosphatase 1 regulation and specificity. FEBS J 280, 596-611 (2013).
Ragusa, M. J. et al. Flexibility in the PP1:spinophilin holoenzyme. FEBS Lett, 585: 36-40 (2011).
Ragusa, M.J. et al. Spinophilin directs protein phosphatase 1 specificity by blocking substrate binding sites. Nat Struct Mol Biol 17, 459-64 (2010).
Reither, G. et al. Chemical activators of protein phosphatase-1 induce calcium release inside intact cells. Chem Biol, 20: 1179-1186 (2013).
Rodriguez, A. et al. A conserved docking surface on calcineurin mediates interaction with substrates and immunosuppressants. Mol Cell 33, 616-26 (2009).
Roy, J. et al. Cracking the phosphatase code: docking interactions determine substrate specificity. Sci Signal 2, re9 (2009).
Rutkowski, D.T. et al. That which does not kill me makes me stronger: adapting to chronic ER stress. Trends Biochem Sci 32, 469-76 (2007).
Saxena, S. et al. A role for motoneuron subtype-selective ER stress in disease manifestations of FALS mice. Nat Neurosci, 12: 627-636 (2009).
Shi, Y. Assembly and structure of protein phosphatase 2A, Sci China C Life Sci 52, 135-46 (2009).
Shi, Y. Serine/threonine phosphatases: mechanism through structure, Cell 139, 468-84 (2009).
Takeuchi, K. et al. Structure of the calcineurin-NFAT complex: defining a T cell activation switch using solution NMR and crystal coordinates. Structure 15, 587-97 (2007).
Terrak, M. et al. Structural basis of protein phosphatase 1 regulation. Nature 429, 780-4 (2004).
Tonks, N.K. et al. Protein tyrosine phosphatases: from genes, to function, to disease. Nat Rev Mol Cell Biol, 7: 833-846 (2006).
Tsaytler, P. Et al. Selective inhibition of a regulatory subunit of protein phosphatase 1 restores proteostasis, Science 332, 91-4 (2011).
Virshup. D.M. et al. From promiscuity to precision: protein phosphatases get a makeover, Mol Cell, 33: 537-545 (2009).
Xing.Y. et al. Structure of protein phosphatase 2A core enzyme bound to tumor-inducing toxins, Cell, 127: 341-353 (2006).

(Continued)

*Primary Examiner* — Maury Audet
*Assistant Examiner* — Fred Reynolds
(74) *Attorney, Agent, or Firm* — Lawson & Weitzen LLP; Sonia K. Guterman; Anna E. Stanford

(57) ABSTRACT

Therapeutic compositions for treatment of protein serine/threonine phosphatase-related diseases are obtained by engineering amino acid sequences that disrupt interaction between the protein serine/threonine phosphatase and a protein inhibitor and are provided herein. Calcineurin and PPI are examples of protein serine/threonine phosphatases. RCAN1 is an inhibitor of calcineurin and is overexpressed in patients with serious diseases, such as Down syndrome and Alzheimer's disease. Molecules that bind RCAN1 at regions that interact with calcineurin selectively modulate functions of calcineurin to treat these diseases. Methods of treating a subject for a protein serine/threonine phosphatase-related disease by administering a molecule having an amino acid sequence selected from the group of SEQ ID NOs: 1-19 are further provided.

5 Claims, 9 Drawing Sheets

(56) References Cited

PUBLICATIONS

Alonso, A. et al. "Protein tyrosine phosphatases in the human genome" Cell, 117: 699-711 (2004).

Aramburu, J. et al. Selective inhibition of NFAT activation by a peptide spanning the calcineurin targeting site of NFAT Mol Cell, 1: 627-637 (1998).

Arron, J. et al. NFAT dysregulation by increased dosage of DSCR1 and DYRK1A on chromosome 21. Nature 441, 595-600 (2006).

Bollen, M. Combinatorial control of protein phosphatase-1. Trends Biochem Sci 26, 426-31 (2001).

Bollen, M. et al. The extended PP1 toolkit: designed to create specificity. Trends Biochem Sci 35, 450-8 (2010).

Boyce, M. et al. A selective inhibitor of eIF2alpha dephosphorylation protects cells from ER stress. Science 307, 935-9 (2005).

Braithwaite, S.P. et al. Protein phosphatases and Alzheimer's disease. Prog Mol Biol Transl Sci 106, 343-79 (2012).

Brush, M. H. et al. Growth arrest and DNA damage-inducible protein GADD34 targets protein phosphatase 1 alpha to the endoplasmic reticulum and promotes dephosphorylation of the alpha subunit of eukaryotic translation initiation factor 2. Mol Cell Biol 23, 1292-303 (2003).

Chan, B. et al. Identification of a peptide fragment of DSCR1 that competitively inhibits calcineurin activity in vitro and in vivo. Proc Natl Acad Sci U S A 102, 13075-80 (2005).

Chatterjee, J. et al. Targeting the untargetable: recent advances in the selective chemical modulation of protein phosphatase-1 activity. Current opinion in chemical biology, 17: 361-368 (2013).

Chatterjee, J. et al. Development of a peptide that selectively activates protein phosphatase-1 in living cells. Angewandte Chemie, 51: 10054-10059 (2012).

Choy M.S. et al. Understanding the antagonism of retinoblastoma protein dephosphorylation by PNUTS provides insights into the PP1 regulatory code. Proc Natl Acad Sci U S A 111, 4097-102 (2014).

Cohen, P.T. Protein phosphatase 1—targeted in many directions. J Cell Sci 115, 241-56 (2002).

Connor, J.H. et al. Growth arrest and DNA damage-inducible protein GADD34 assembles a novel signaling complex containing protein phosphatase 1 and inhibitor 1. Mol Cell Biol 21, 6841-50 (2001).

Dancheck, B. et al. Detailed structural characterization of unbound protein phosphatase 1 inhibitors. Biochemistry, 47: 12346-12356 (2008).

Dancheck, B. et al. Molecular investigations of the structure and function of the protein phosphatase 1-spinophilin-inhibitor 2 heterotrimeric complex. Biochemistry 50, 1238-46 (2011).

Francis, D. M. et al. Structural basis of p38alpha regulation by hematopoietic tyrosine phosphatase. Nat Chem Biol 7, 916-24 (2011).

Fuentes, J. J. et al. DSCR1, overexpressed in Down syndrome, is an inhibitor of calcineurin-mediated signaling pathways, Hum Mol Genet 9, 1681-90 (2000).

Fullwood, M.J. et al. Targeting phosphorylation of eukaryotic initiation factor-2alpha to treat human disease. Prog Mol Biol Transl Sci 106, 75-106 (2012).

Gehringer, M.M. Microcystin-LR and okadaic acid-induced cellular effects: a dualistic response. FEBS Lett, 557: 1-8(2004).

Goldberg, J. et al. Three-dimensional structure of the catalytic subunit of protein serine/threonine phosphatase-1. Nature, 376: 745-753 (1995).

Grigoriu, S. et al. The molecular mechanism of substrate engagement and immunosuppressant inhibition of calcineurin. PLoS Biol 11, e1001492 (2013).

Harding, H.P. et al. Ppp1r15 gene knockout reveals an essential role for translation initiation factor 2 alpha (eIF2alpha) dephosphorylation in mammalian development. Proc Natl Acad Sci USA, 106: 1832-1837 (2009).

Hendrickx, A et al. Docking motif-guided mapping of the interactome of protein phosphatase-1. Chem Biol 16, 365-71 (2009).

Hilioti, Z. et al. The RCN family of calcineurin regulators. Biochem Biophys Res Commun 311, 1089-93 (2003).

Hurley, T.D. et al. Structural basis for regulation of protein phosphatase 1 by inhibitor-2. J Biol Chem 282, 28874-83 (2007).

Jousse, C. et al. Inhibition of a constitutive translation initiation factor 2alpha phosphatase. CReP, promotes survival of stressed cells. J Cell Biol, 163: 767-775 (2003).

Julien, S. G. et al. Inside the human cancer tyrosine phosphatome. Nature reviews. Cancer, 11: 35-49 (2011).

Katz, C. et al. Studying protein-protein interactions using peptide arrays. Chem Soc Rev 40, 2131-45 (2011).

Kelker, M.S. et al. Crystal structures of protein phosphatase-1 bound to nodularin-R and tautomycin: a novel scaffold for structure-based drug design of serine/threonine phosphatase inhibitors. J Mol Biol 385, 11-21 (2009).

Khanna, A. et al. Cancerous inhibitor of protein phosphatase 2A, an emerging human oncoprotein and a potential cancer therapy target. Cancer research, 73: 6548-6553 (2013).

Kingsbury, T.J. et al. A conserved family of calcineurin regulators. Genes Dev 14, 1595-604 (2000).

Kissinger, C.R. et al. Crystal structures of human calcineurin and the human FKBP12-FK506-calcineurin complex. Nature 378, 641-4 (1995).

Kojima, E. et al. The function of GADD34 is a recovery from a shutoff of protein synthesis induced by ER stress: elucidation by GADD34-deficient mice. FASEB J, 17: 1573-1575 (2003).

Li, H. et al. Structure of calcineurin in complex with PVIVIT peptide: portrait of a low-affinity signalling interaction. J Mol Biol 369, 1296-1306 (2007).

Li, H. et al. Interaction of calcineurin with substrates and targeting proteins. Trends Cell Biol 21, 91-103 (2011).

Li, H.et al. Balanced interactions of calcineurin with AKAP79 regulate Ca2+-calcineurin-NFAT signaling. Nat Struct Mol Biol, 19: 337-345 (2012).

Manning, G., The protein kinase complement of the human genome. Science, 298: 1912-1934 (2002).

Marsh, J.A. et al. Structural diversity in free and bound states of intrinsically disordered protein phosphatase 1 regulators. Structure 18, 1094-103 (2010).

Martinez-Martinez, S. et al. The RCAN carboxyl end mediates calcineurin docking-dependent inhibition via a site that dictates binding to substrates and regulators. Proc Natl Acad Sci U S A 106, 6117-22 (2009).

Matus, S. et al. Protein folding stress in neurodegenerative diseases: a glimpse into the ER. Curr Opin Cell Biol 23, 239-52 (2011).

Maynes, J. T. et al. Crystal structure of the tumor-promoter okadaic acid bound to protein phosphatase-1. J Biol Chem, 276: 44078-44082 (2001).

Mehta, S. et al. Domain architecture of the regulators of calcineurin (RCANs) and identification of a divergent RCAN in yeast, Mol Cell Biol 29, 2777-93 (2009).

Meiselbach, H. Structural analysis of the protein phosphatase 1 docking motif: molecular description of binding specificities identifies interacting proteins. Chem Biol 13, 49-59 (2006).

Minnebo, N. et al. NIPP1 maintains EZH2 phosphorylation and promoter occupancy at proliferation-related target genes. Nucleic Acids Res, 41: 842-854 (2013).

Mohi, M. G. et al., The role of Shpt (PTPN11) in cancerCurrent opinion in genetics & development, 17: 23-30 (2007).

Mustelin, T. et al. Protein tyrosine phosphatases and the immune response. Nature reviews. Immunology, 5: 43-57 (2005).

Nairn A. C. et al. The role of DARPP-32 in the actions of drugs of abuse Neuropharmacology. 47 Suppl 1, 14-23 (2004).

Nova, L. et al. Feedback inhibition of the unfolded protein response by GADD34-mediated dephosphorylation of eIF2alpha. J Cell Biol, 153: 1011-1022 (2001).

O'Connell, N. et al. The Molecular Basis for Substrate Specificity of the Nuclear NIPP1:PP1 Holoenzyme. Structure 20, 1746-56 (2012).

\* cited by examiner

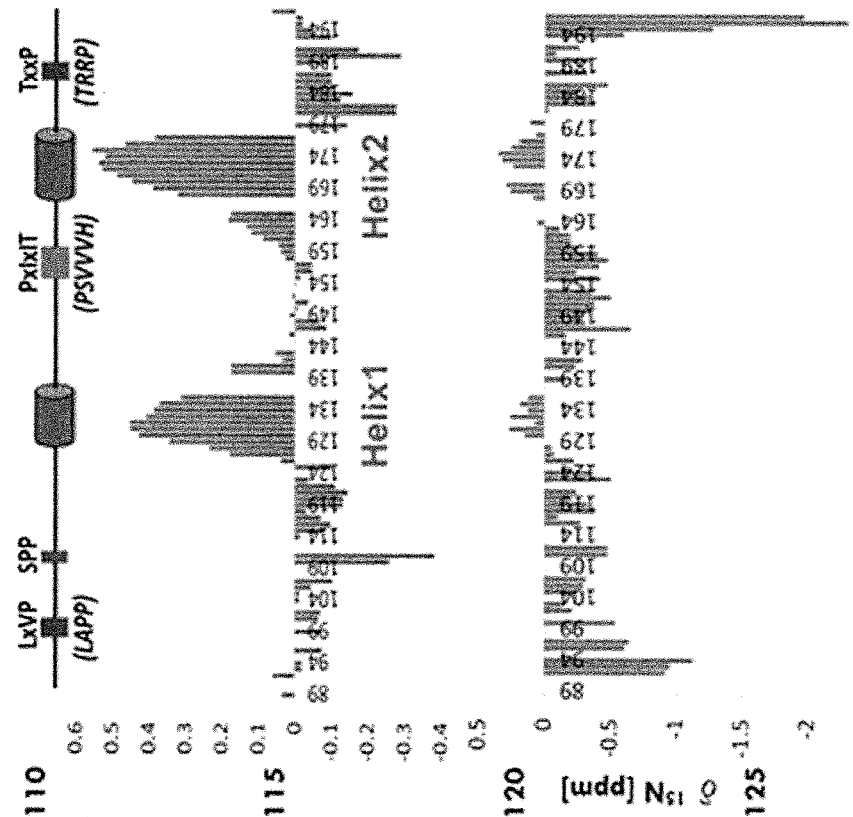
Figure 3B
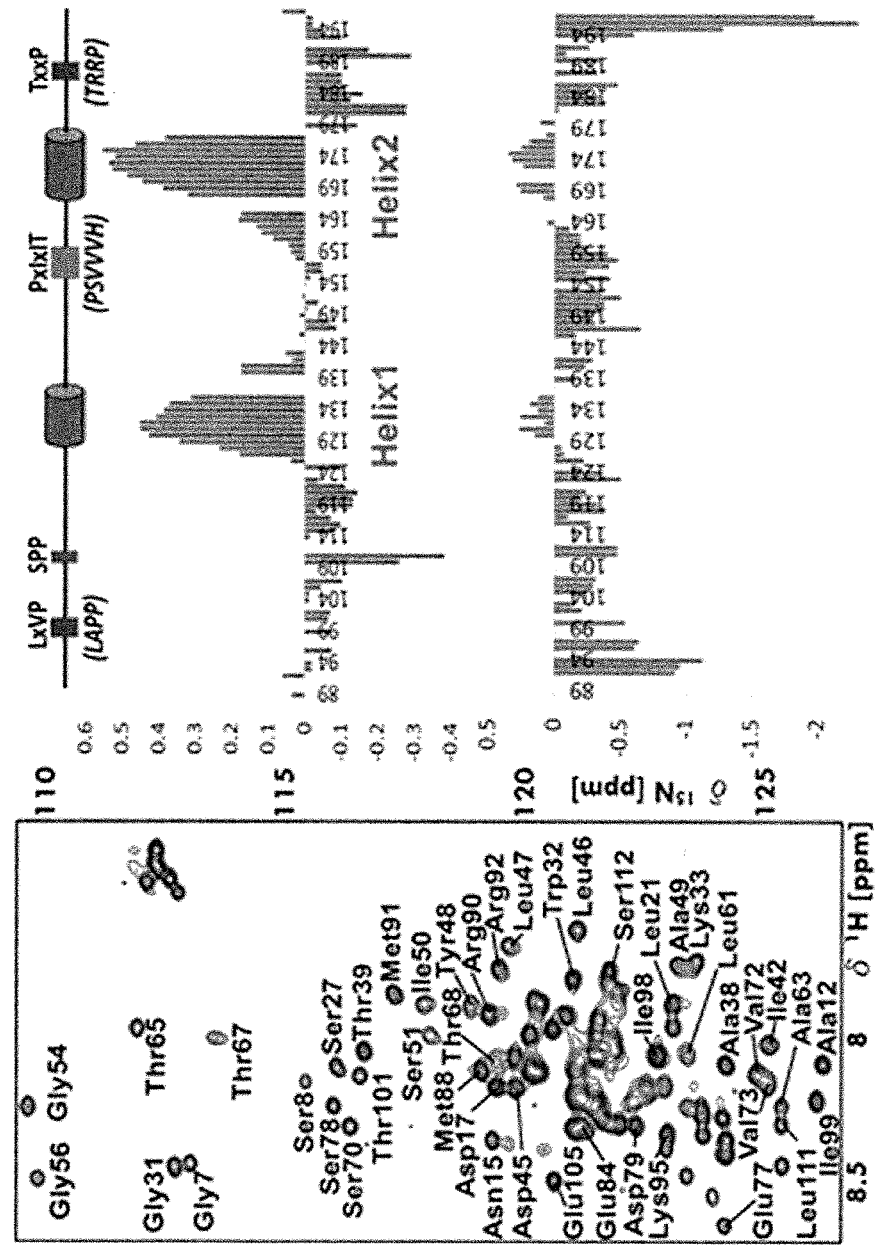
Figure 3A
Figure 3C

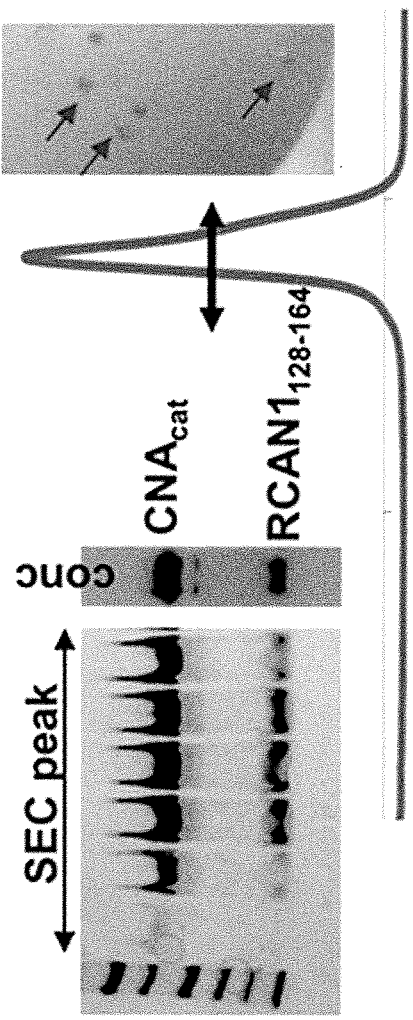
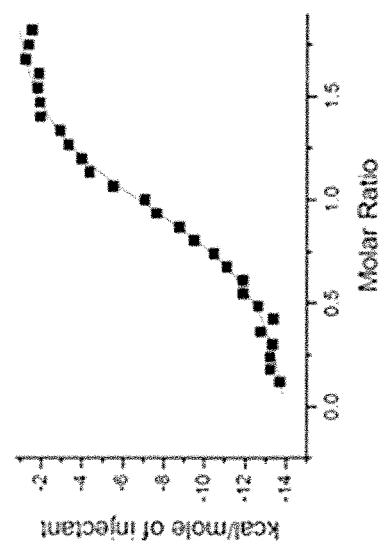
Figure 4A
Figure 4B

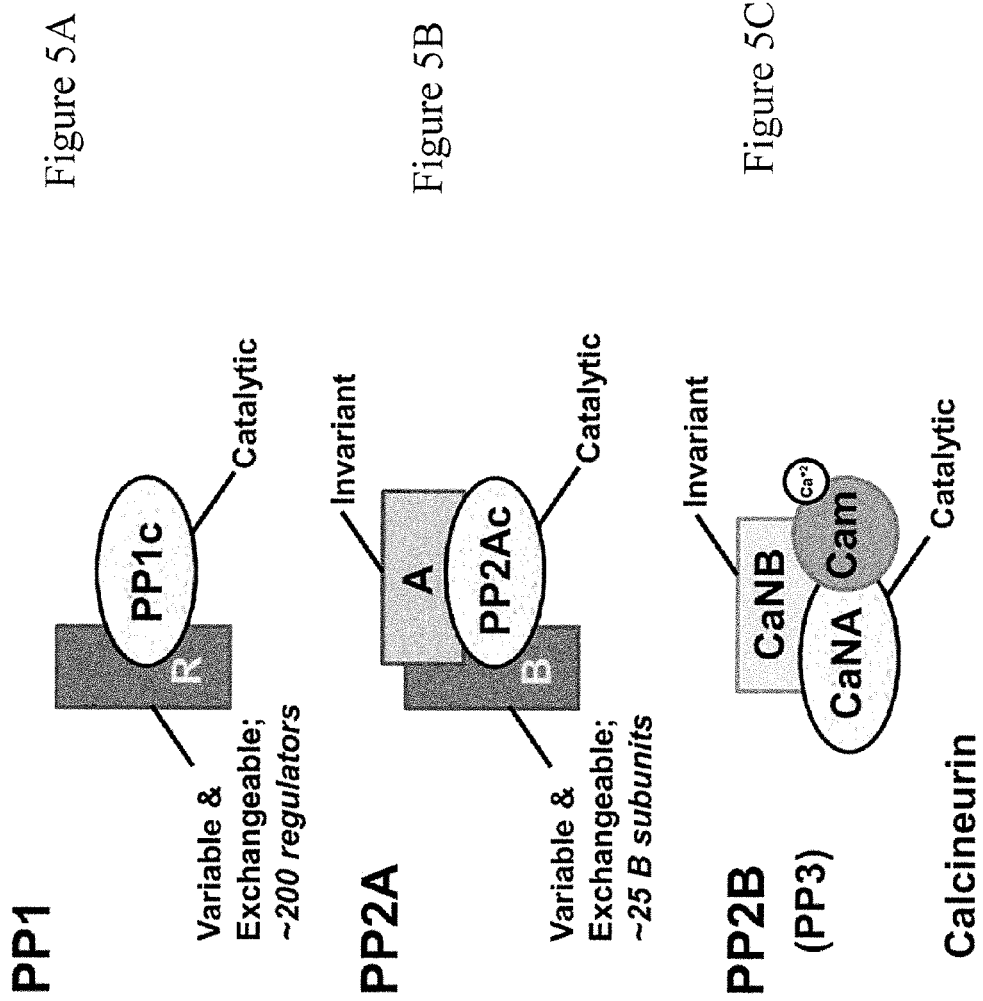

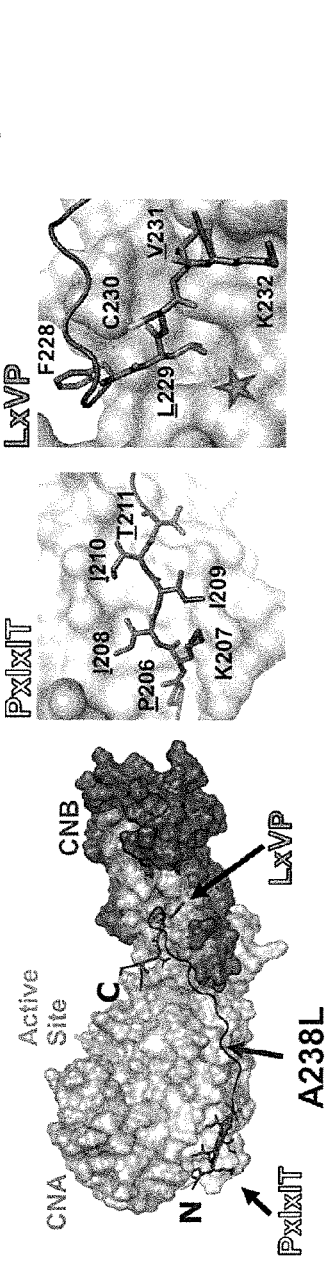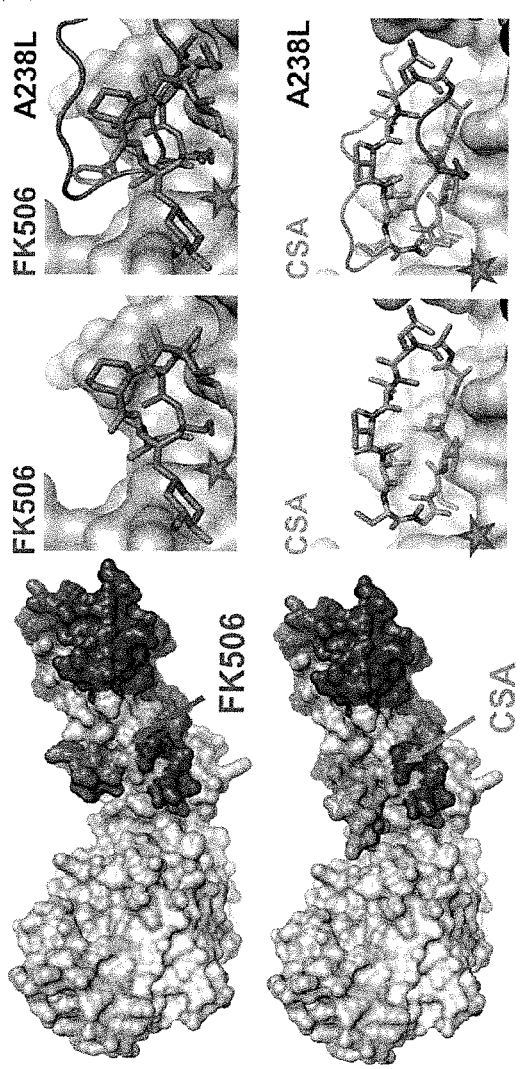

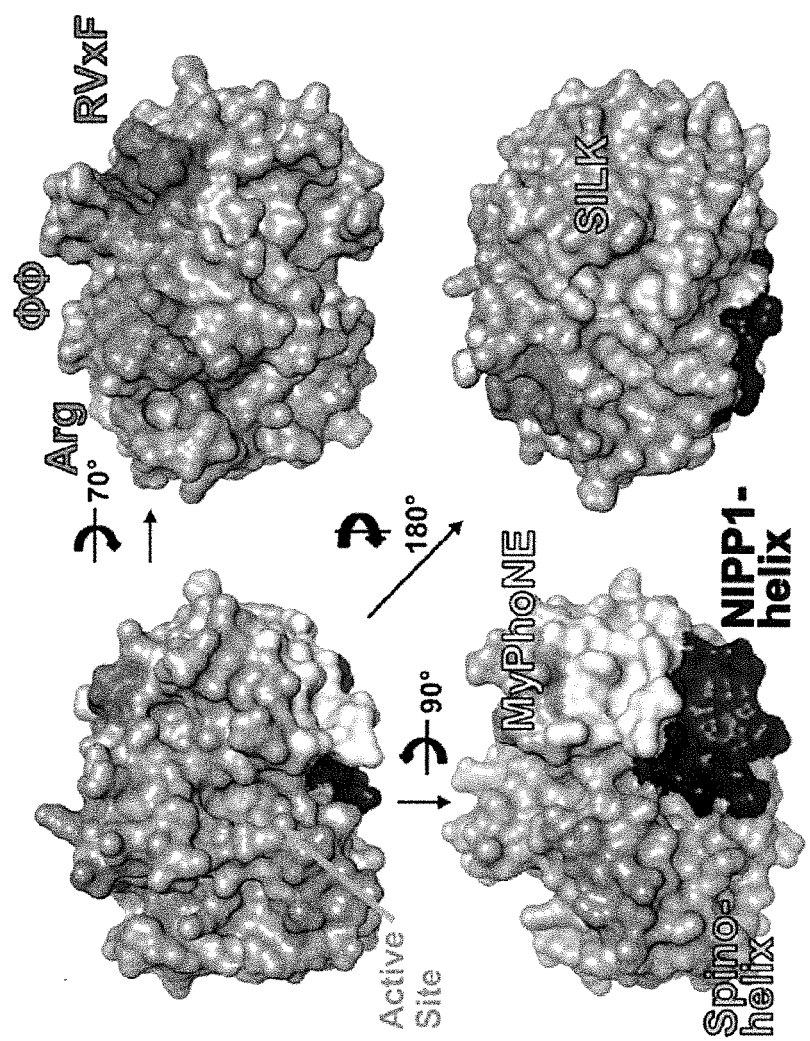

SEQUENCE LISTING

<160> NUMBER OF SEQ ID NOS: 19

<210> SEQ ID NO 1
<211> LENGTH: 197
<212> TYPE: PRT
<213> ORGANISM: Artificial Sequence
<220> FEATURE:
<223> OTHER INFORMATION: The sequence was designed and synthesized

<400> SEQUENCE: 1

Met Glu Glu Val Asp Leu Gln Asp Leu Pro Ser Ala Thr Ile Ala Cys
1               5                   10                  15

His Leu Asp Pro Arg Val Phe Val Asp Gly Leu Cys Arg Ala Lys Phe
            20                  25                  30

Glu Ser Leu Phe Arg Thr Tyr Asp Lys Asp Ile Thr Phe Gln Tyr Phe
        35                  40                  45

Lys Ser Phe Lys Arg Val Arg Ile Asn Phe Ser Asn Pro Phe Ser Ala
    50                  55                  60

Ala Asp Ala Arg Leu Gln Leu His Lys Thr Glu Phe Leu Gly Lys Glu
65                  70                  75                  80

Met Lys Leu Tyr Phe Ala Gln Thr Leu His Ile Gly Ser Ser His Leu
                85                  90                  95

Ala Pro Pro Asn Pro Asp Lys Gln Phe Leu Ile Ser Pro Pro Ala Ser
            100                 105                 110

Pro Pro Val Gly Trp Lys Gln Val Glu Asp Ala Thr Pro Val Ile Asn
        115                 120                 125

Tyr Asp Leu Leu Tyr Ala Ile Ser Lys Leu Gly Pro Gly Glu Lys Tyr
    130                 135                 140

Glu Leu His Ala Ala Thr Asp Thr Thr Pro Ser Val Val Val His Val
145                 150                 155                 160

Cys Glu Ser Asp Gln Glu Lys Glu Glu Glu Met Glu Arg Met
                165                 170                 175

Arg Arg Pro Lys Pro Lys Ile Ile Gln Thr Arg Arg Pro Glu Tyr Thr
            180                 185                 190

Pro Ile His Leu Ser
        195

<210> SEQ ID NO 2
<211> LENGTH: 109
<212> TYPE: PRT
<213> ORGANISM: Artificial Sequence
<220> FEATURE:
<223> OTHER INFORMATION: The sequence was designed and synthesized

<400> SEQUENCE: 2

Leu His Ile Gly Ser Ser His Leu Ala Pro Pro Asn Pro Asp Lys Gln
1               5                   10                  15

Phe Leu Ile Ser Pro Pro Ala Ser Pro Pro Val Gly Trp Lys Gln Val
            20                  25                  30

Glu Asp Ala Thr Pro Val Ile Asn Tyr Asp Leu Leu Tyr Ala Ile Ser
        35                  40                  45

Lys Leu Gly Pro Gly Glu Lys Tyr Glu Leu His Ala Ala Thr Asp Thr
    50                  55                  60

Thr Pro Ser Val Val Val His Val Cys Glu Ser Asp Gln Glu Lys Glu
65                  70                  75                  80

Glu Glu Glu Met Glu Arg Met Arg Arg Pro Lys Pro Lys Ile Ile
                85                  90                  95

Gln Thr Arg Arg Pro Glu Tyr Thr Pro Ile His Leu Ser
            100                 105

<210> SEQ ID NO 3
<211> LENGTH: 7
<212> TYPE: PRT

```
<213> ORGANISM: Artificial Sequence
<220> FEATURE:
<223> OTHER INFORMATION: The sequence was designed and synthesized

<400> SEQUENCE: 3

Ser Pro Pro Ala Ser Pro Pro
1               5

<210> SEQ ID NO 4
<211> LENGTH: 9
<212> TYPE: PRT
<213> ORGANISM: Artificial Sequence
<220> FEATURE:
<223> OTHER INFORMATION: The sequence was designed and synthesized

<400> SEQUENCE: 4

Asp Leu Leu Tyr Ala Ile Ser Lys Leu
1               5

<210> SEQ ID NO 5
<211> LENGTH: 3
<212> TYPE: PRT
<213> ORGANISM: Artificial Sequence
<220> FEATURE:
<223> OTHER INFORMATION: The sequence was designed and synthesized

<400> SEQUENCE: 5

Glu Leu His
1

<210> SEQ ID NO 6
<211> LENGTH: 14
<212> TYPE: PRT
<213> ORGANISM: Artificial Sequence
<220> FEATURE:
<223> OTHER INFORMATION: The sequence was designed and synthesized

<400> SEQUENCE: 6

Glu Lys Glu Glu Glu Glu Glu Met Glu Arg Met Arg Arg Pro
1               5                   10

<210> SEQ ID NO 7
<211> LENGTH: 37
<212> TYPE: PRT
<213> ORGANISM: Artificial Sequence
<220> FEATURE:
<223> OTHER INFORMATION: The sequence was designed and synthesized

<400> SEQUENCE: 7

Asn Tyr Asp Leu Leu Tyr Ala Ile Ser Lys Leu Gly Pro Gly Glu Lys
1               5                   10                  15

Tyr Glu Leu His Ala Ala Thr Asp Thr Thr Pro Ser Val Val Val His
            20                  25                  30

Val Cys Glu Ser Asp
        35

<210> SEQ ID NO 8
<211> LENGTH: 26
<212> TYPE: PRT
<213> ORGANISM: Artificial Sequence
<220> FEATURE:
<223> OTHER INFORMATION: The sequence was designed and sythesized

<400> SEQUENCE: 8

Asn Tyr Asp Leu Leu Tyr Ala Ile Ser Lys Leu Gly Pro Gly Glu Lys
1               5                   10                  15
```

```
Tyr Glu Leu His Ala Ala Thr Asp Thr Thr
            20                  25
```

```
<210> SEQ ID NO 9
<211> LENGTH: 6
<212> TYPE: PRT
<213> ORGANISM: Artificial Sequence
<220> FEATURE:
<223> OTHER INFORMATION: The sequence was designed and synthesized
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 9

Pro Xaa Ile Xaa Ile Thr
1               5
```

```
<210> SEQ ID NO 10
<211> LENGTH: 4
<212> TYPE: PRT
<213> ORGANISM: Artificial Sequence
<220> FEATURE:
<223> OTHER INFORMATION: The sequence was designed and synthesized
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 10

Leu Xaa Val Pro
1
```

```
<210> SEQ ID NO 11
<211> LENGTH: 4
<212> TYPE: PRT
<213> ORGANISM: Artificial Sequence
<220> FEATURE:
<223> OTHER INFORMATION: The sequence was designed and synthesized
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 11

Thr Xaa Xaa Pro
1
```

```
<210> SEQ ID NO 12
<211> LENGTH: 4
<212> TYPE: PRT
<213> ORGANISM: Artificial Sequence
<220> FEATURE:
<223> OTHER INFORMATION: The sequence was designed and synthesized

<400> SEQUENCE: 12

Leu Ala Pro Pro
1
```

```
<210> SEQ ID NO 13
<211> LENGTH: 6
<212> TYPE: PRT
<213> ORGANISM: Artificial Sequence
<220> FEATURE:
<223> OTHER INFORMATION: The sequence was designed and synthesized
```

```
<400> SEQUENCE: 13

Pro Ser Val Val His
1               5

<210> SEQ ID NO 14
<211> LENGTH: 4
<212> TYPE: PRT
<213> ORGANISM: Artificial Sequence
<220> FEATURE:
<223> OTHER INFORMATION: The sequence was designed and synthesized

<400> SEQUENCE: 14

Thr Arg Arg Pro
1

<210> SEQ ID NO 15
<211> LENGTH: 4
<212> TYPE: PRT
<213> ORGANISM: Artificial Sequence
<220> FEATURE:
<223> OTHER INFORMATION: The sequence was designed and synthesized
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 15

Arg Val Xaa Phe
1

<210> SEQ ID NO 16
<211> LENGTH: 5
<212> TYPE: PRT
<213> ORGANISM: Artificial Sequence
<220> FEATURE:
<223> OTHER INFORMATION: The sequence was designed and synthesized

<400> SEQUENCE: 16

His Leu Ala Pro Pro
1               5

<210> SEQ ID NO 17
<211> LENGTH: 5
<212> TYPE: PRT
<213> ORGANISM: Artificial Sequence
<220> FEATURE:
<223> OTHER INFORMATION: The sequence was designed and synthesized

<400> SEQUENCE: 17

Ala Ala Ala Ala Ala
1               5

<210> SEQ ID NO 18
<211> LENGTH: 6
<212> TYPE: PRT
<213> ORGANISM: Artificial Sequence
<220> FEATURE:
<223> OTHER INFORMATION: The sequence was designed and synthesized

<400> SEQUENCE: 18

Ala Ser Ala Val Ala Ala
1               5

<210> SEQ ID NO 19
<211> LENGTH: 6
<212> TYPE: PRT
```

```
<213> ORGANISM: Artificial Sequence
<220> FEATURE:
<223> OTHER INFORMATION: The sequence was designed and synthesized

<400> SEQUENCE: 19

Pro Val Ile Val Ile Thr
1               5
```

METHOD AND COMPOSITIONS FOR TREATMENT OF CALCINEURIN-RELATED DISEASES

RELATED APPLICATIONS

This application claims the benefit of U.S. provisional application 62/033,766 filed Aug. 6, 2014 in the U.S. Patent and Trademark Office, which is hereby incorporated by reference in its entirety.

GOVERNMENT SUPPORT CLAUSE

This invention was made with government support under 1R01NS091336 awarded by the National Institutes of Health. The government has certain rights in the invention.

TECHNICAL BACKGROUND

Therapeutic methods and compositions for treatment of calcineurin-related diseases by engineering therapeutic amino acid sequences that disrupt interaction between calcineurin and a protein inhibitor are shown herein.

BACKGROUND

Phosphorylation is a nearly ubiquitous and reversible post-translational modifications in cells. See, Olsen et al., *Sci Signal*, 3 (2010). Tight regulation of phosphorylation of highly dynamic, interacting proteins is a key mechanism used by cells to communicate external signals from the membrane to the nucleus. The enzymes responsible for controlling the phosphorylation state of the cell are kinases, which catalyze the transfer the γ-phosphate moiety of ATP to substrates, and phosphatases. Phosphatases catalyze the reverse reaction, which is the removal of the phosphate moiety from phosphorylated substrates. Thus, phosphatases dynamically reverse the effects of kinases. Because phosphorylation is critical for biological processes from cell growth to differentiation to development, the location and duration of the reciprocal actions of kinases and phosphatases is regulated both temporally and spatially within the cell. However, when regulation is disrupted, dysregulation of phosphorylation signaling ensues and the consequence is almost always disease See, Braithwaite, *Progress in molecular biology and translational science*, 106: 343-379 (2012); Tonks et al., *Nat Rev Mol Cell Biol*, 7: 833-846 (2006); Mustelin et al., *Nature reviews. Immunology*, 5: 43-57 (2005); Nairn et al., *Neuropharmacology*, 47 Suppl 1, 14-23 (2004); Mohi et al., *Current opinion in genetics & development*, 17: 23-30 (2007); Julien et al., *Nature reviews. Cancer*, 11: 35-49 (2011).

Protein phosphorylation is a post-translational modification that regulates about 70% of all eukaryotic proteins including many essential signaling cascades in neurons. See, Olsen et al. *Sci Signal* 3(104): ra3, 2010. The specific and reciprocal relationship between protein kinases and protein phosphatases (PSPs) is essential for understanding control and modulation of neurological signaling pathways. Signaling cascade integration is driven by protein phosphatases rather than by kinases, specifically by protein phosphatase 1 (PP1), protein phosphatase 2A (PP2A), and protein phosphatase 2B (PP2B), otherwise known as PP3 or calcineurin. See, Peti et al., *FEBS J* 280:596-611 (2013); Braithwaite et al., *Prog Mol Biol Transl Sci* 106: 343-79 (2012).

Prior to the invention herein, PSPs and PTPs were thought to be unattainable drug targets because natural product inhibitors of PSP active sites are lethal. Further, the active sites of PTPs are conserved and charged creating a challenge for development of PTP inhibitors that are selective. However, the strategy implemented herein has resulted in engineering of an amino acid sequence that disrupts the interaction between a protein inhibitor and PSPs.

In the human genome, a large number (428) of genes encode ser/thr kinases, yet only about 40 genes encode PSPs. Yet, PSPs outnumber kinases at a ratio of about 40:418. See, Bollen et al. *Trends Biochem Sci* 35: 450-8 (2010); Virshup et al., *Mol Cell*, 33: 537-545 (2009); Shi et al., *Cell*, 139: 468-484 (2009); Bollen et al., *Trends Biochem Sci*, 26: 426-431 (2001); See, Bollen et al., *Trends Biochem Sci*, 35 (2010) 450-458; Peti et al., *FEBS J*, 280: 596-611 (2013); Li et al., *Trends Cell Biol*, 21: 91-103 (2011); Roy et al., *Sci Signal*, 2, re9 (2009). Those of ordinary skill in the art of ser/thr phosphatase regulation have previously thought that PSPs function mainly as housekeeping enzymes, however the invention herein shows that this view is incorrect. See, Bollen et al., *Trends Biochem Sci* 26, 426-31 (2001); Bollen et al., *Trends Biochem Sci* 35, 450-8 (2010); Cohen, *J Cell Sci* 115, 241-56 (2002); and Roy et al., *Sci Signal* 2, re9 (2009).

In the human genome, there is a near 1:1 ratio of PTPs (107) to kinases (90). See, Tonks et al., *Nat Rev Mol Cell Biol*, 7: 833-846 (2006); Manning et al., *Science*, 298: 1912-1934 (2002); Alonso et al., *Cell*, 117: 699-711 (2004). In contrast, the serine/threonine phosphatases (PSPs) are woefully outnumbered by their abundant kinase counterparts. See, Virshup et al., *Mol Cell*, 33: 537-545 (2009); Shi et al., *Cell*, 139: 468-484 (2009); Bollen et al., *Trends Biochem Sci*, 26: 426-431 (2001); See, Bollen et al., *Trends Biochem Sci*, 35 (2010) 450-458; Peti et al., *FEBS J*, 280: 596-611 (2013); Li et al., *Trends Cell Biol*, 21: 91-103 (2011); Roy et al., *Sci Signal*, 2, re9 (2009). Thus, while PTPs have been considered to be viable drug targets, PSPs have been viewed as 'house-keeping' enzymes, with only a limited chance for drug selectivity. This assessment is due in large part because the active sites of the three most abundant and well-studied PSPs: PP1, PP2A, and calcineurin are 100% conserved. Therefore, active site inhibitors would likely not be selective. See, FIG. 5; Peti et al., *FEBS J*, 280: 596-611 (2013); Li et al., *Trends Cell Biol*, 21: 91-103 (2011); Roy et al., *Sci Signal*, 2, re9 (2009). This has been confirmed by the discovery of natural product PSP inhibitors, such as microcystin, nodularin, okadaic acid, and tautomycin among others, which inhibit all three phosphatases with only a slight preference of one over another. See, Goldberg et al., *Nature*, 376: 745-753 (1995); Kelker et al., *J Mol Biol*, 385: 11-21 (2009); Maynes et al., *J Biol Chem*, 276: 44078-44082 (2001); Xing et al., *Cell*, 127: 341-353 (2006).

Calcineurin is ubiquitously expressed throughout the body, and is particularly abundant in the brain. Calcineurin regulates development, synaptic plasticity, learning, and memory formation by dephosphorylating a variety of protein substrates in response to $Ca^{2+}$. See, Shi et al. *Cell* 139:468-84 (2009); Shi et al. *Sci China C Life Sci* 52: 135-46 (2009). PSPs function as holoenzymes in vivo, for example calcineurin requires a B-subunit and calmodulin for activity. See, Bollen et al. *Trends Biochem Sci* 35: 450-8 (2010).

Calcineurin has two subunits: a catalytic A subunit (CNA) which is highly conserved from yeast to humans and has an active site identical to the active site of PP1, and the regulatory B subunit (CNB) that resembles calmodulin and binds four $Ca^{2+}$ ions. See, Kissinger et al., *Nature* 378: 641-4

(1995). CNA binds CNB via an extended helix α14, the CNB-binding helix, which extends away from the globular catalytic core.

There is a need for novel compounds to regulate phosphatase function of calcineurin to treat brain conditions.

SUMMARY

In various embodiments, the invention provides a method for treating a protein serine/threonine phosphatase-related disease, that includes the steps of administering to a subject a composition that disrupts interaction between a protein inhibitor and the protein serine/threonine phosphatase in the subject, in which the protein inhibitor inhibits at least one function of the protein serine/threonine phosphatase; increasing the function of the protein serine/threonine phosphatase compared to the function prior to the administering and decreasing a symptom of the protein serine/threonine phosphatase-related disease, thereby treating the subject for the disease. In certain embodiments, the protein serine/threonine phosphatase is at least one selected from the group containing PP1, PP2, and calcineurin.

In certain embodiments, the protein inhibitor is substantially identical to regulator of calcineurin 1 (RCAN1) or a portion thereof. In an embodiment, the protein inhibitor is RCAN1. In an embodiment, the protein inhibitor is not a substrate for phosphatase function of the protein serine/threonine phosphatase. In an embodiment, the protein inhibitor is a substrate for phosphatase function of the protein serine/threonine phosphatase. In certain embodiments, the composition disrupts the interaction between a protein inhibitor and the protein serine/threonine phosphatase by binding of the protein inhibitor to the protein serine/threonine phosphatase at a location distal to a catalytic site. In an embodiment, the method uses a composition that further includes a poly-arginine (R) amino acid sequence at the N-terminus. In certain embodiments, the protein serine/threonine phosphatase-related disease is at least one disease selected from the group consisting of: Alzheimer's disease, Down syndrome, Parkinson's disease, amyotrophic lateral sclerosis, Huntington's disease, spongiform encephalopathies, familial amyloidotic polyneuropathy, type II diabetes, spinocerebral ataxia type 6, familial British dementia, Fabry's disease, spinobulbular muscular atrophy, ataxia, Wilson disease, atrial amyloidosis of heart, dentatorubral pallidoluysian atrophy, haemodialysis-associated amyloidosis, hereditary cerebral amyloid angiopathy, Gaucher's disease, medullary carcinoma of thyroid, hereditary cerebral amyloid angiopathy, cystic fibrosis, Marfan syndrome, fragile X syndrome, fragile XE syndrome, Finnish type familial amyloidosis, Alexander disease, light chain amyloidosis, Machado-Joseph disease, hereditary systemic amyloidosis, myotonic dystrophy, aquaporin-vasopressin-1, cancer, prion diseases, retinitis pigmentosa protein, secondary systemic amyloidosis, amyotrophic lateral sclerosis, frontotemporal dementia, and familial amyloid polyneuropathy.

In certain embodiments, the method includes the step of analyzing amount of binding by the composition to a portion of RCAN1 including at least one amino acid sequence selected from the group consisting of: amino acid positions 89-197, amino acid positions 108-114, amino acid positions 145-147, amino acid positions 130-138, amino acid positions 166-179, and conservative substitutions thereof. In certain embodiments, the method includes the step of analyzing the amount of binding of a portion of the protein inhibitor including at least one amino acid sequence selected from the group consisting of: SEQ ID NOs: 1-19, and conservative substitutions thereof by the composition. The sequence listing material in computer readable form ASCII text file (8 kilobytes) created Jul. 30, 2015 entitled "02268097_SequenceListing", containing sequence listings numbers 1-19, has been electronically filed herewith and is incorporated by reference herein in its entirety.

In certain embodiments, the method includes prior to administering the step of formulating the composition to include at least one portion substantially identical to calmodulin and to include $Ca^{2+}$ ions, such that the portion has affinity to bind the protein serine/threonine phosphatase thereby disengaging the protein serine/threonine phosphatase auto-inhibitory domain and increasing function of the protein serine/threonine phosphatase. In certain embodiments, the composition includes at least one of a targeting protein or a scaffolding protein. In certain embodiments, the method includes, prior to administering the step of formulating, the composition to modulate specificity of the protein serine/threonine phosphatase in the subject by directing substrates away from the protein serine/threonine phosphatase. In certain embodiments, the method includes prior to administering the step of formulating the composition to include bind to the protein inhibitor thereby increasing dephosphorylation of NFATs, in which the NFATs translocate into the nucleus and initiate transcription. In certain embodiments, the composition includes at least one amino acid sequence selected from the group of: SEQ ID NOs: 1-19, and conservative substitutions thereof.

An aspect of the invention provides a composition for treating a protein serine/threonine phosphatase-related disease includes a molecule that binds a protein inhibitor of the protein serine/threonine phosphatase, in which a function of the protein serine/threonine phosphatase is increased. In certain embodiments, the molecule has affinity to bind at least one amino acid sequence selected from the group of: SEQ ID NOs: 1-19, and conservative substitutions thereof. In an embodiment, the molecule is expressed as a GST-fusion or a MBP-fusion protein. In an embodiment, the molecule includes a helical structure. In certain embodiments, the molecule includes at least one amino acid sequence selected from the group consisting of: SEQ ID NOs: 1-19, and conservative substitutions thereof. In an embodiment, the protein inhibitor is substantially identical to RCAN1. In an embodiment, the protein inhibitor is not a substrate protein. In an embodiment, the protein inhibitor is a substrate protein. In an embodiment, the composition has affinity to bind a portion of the protein serine/threonine phosphatase at a location distal to a catalytic site. The composition has a poly-arginine (R) amino acid sequence on the N-terminus of at least one peptide in the composition.

In an embodiment, the protein serine/threonine phosphatase-related disease is at least one disease selected from the group consisting of: Alzheimer's disease, Down syndrome, Parkinson's disease, amyotrophic lateral sclerosis, Huntington's disease, spongiform encephalopathies, familial amyloidotic polyneuropathy, type II diabetes, spinocerebral ataxia type 6, familial British dementia, Fabry's disease, spinobulbular muscular atrophy, ataxia, Wilson disease, atrial amyloidosis of heart, dentatorubral pallidoluysian atrophy, haemodialysis-associated amyloidosis, hereditary cerebral amyloid angiopathy, Gaucher's disease, medullary carcinoma of thyroid, hereditary cerebral amyloid angiopathy, cystic fibrosis, Marfan syndrome, fragile X syndrome, fragile XE syndrome, Finnish type familial amyloidosis, Alexander disease, light chain amyloidosis, Machado-Joseph disease, hereditary systemic amyloidosis, myotonic dystrophy, aquaporin-vasopressin-1, cancer, prion diseases, retinitis pigmentosa protein, secondary systemic amyloidosis, amyotrophic lateral sclerosis, frontotemporal dementia, and familial amyloid polyneuropathy.

In certain embodiments, the composition has affinity to bind a portion of RCAN1 including at least one amino acid sequence selected from the group consisting of: amino acid positions 89-197, amino acid positions 108-114, amino acid positions 145-147, amino acid positions 130-138, and amino acid positions 166-179. In certain embodiments, the composition includes a peptide that is substantially identical to a portion of calmodulin, in which the portion has affinity to bind the protein serine/threonine phosphatase thereby disengaging the protein serine/threonine phosphatase autoinhibitory domain and increasing the function of the protein serine/threonine phosphatase. In an embodiment, the composition includes at least one of a targeting protein or a scaffolding protein. In an embodiment, the targeting protein or scaffolding protein directs substrates toward the protein serine/threonine phosphatase. In an embodiment, the composition disrupts a complex of the protein serine/threonine phosphatase bound to the protein inhibitor thereby exposing a catalytic site of the protein serine/threonine phosphatase. In an embodiment, the composition has affinity to bind the protein inhibitor thereby increasing the amount of dephosphorylation of nuclear factor of activated T cells (NFATs).

Various aspects of the invention provide a method for identifying a peptide that disrupts interactions between a protein serine/threonine phosphatase and at least one protein inhibitor, the method including preparing a peptide library including amino acid sequences selected from the group consisting of: SEQ ID NOs: 1-19, and conservative substitutions thereof; contacting a protein serine/threonine phosphatase or a portion thereof including a catalytic domain in a mixture with the protein inhibitor with the peptide library; and isolating peptides that disrupt interaction between a protein serine/threonine phosphatase and the protein inhibitor. In certain embodiments, the method includes the step of determining the amino acid sequence of the peptides and mutating at least one amino acid residue within or surrounding the amino acid sequence. In certain embodiments, the method includes the step of changing binding affinity between the peptide that binds and peptides having a mutated amino acid sequence to determine amino acid positions that are necessary for inhibition. In certain embodiments, the amino acid residue mutation is at least one selected from the group consisting of: K to A, Q to A, E to R, K to E, E to A, R to A, R to D, H to A, D to A, R to A, and R to D, and Y to A.

An aspect of the invention provides a method of making a composition for treating a protein serine/threonine phosphatase-related disease, the method including synthesizing a molecule having at least one amino acid sequence selected from the group consisting of: SEQ ID NOs: 1-19, and conservative substitutions thereof; and disrupting interaction by the molecule, between a protein inhibitor and a protein serine/threonine phosphatase. In an embodiment, synthesizing is performed using at least one technique selected from the group consisting of: solid state synthesis, in vivo using a display vector, in vitro, and solution phase synthesis. Protein serine/threonine phosphatase-related diseases include brain-related conditions such as Alzheimer's disease, Down syndrome, Parkinson's disease, amyotrophic lateral sclerosis, Huntington's disease, spongiform encephalopathies, familial amyloidotic polyneuropathy, type II diabetes, spinocerebral ataxia type 6, familial British dementia, Fabry's disease, spinobulbinar muscular atrophy, ataxia, Wilson disease, atrial amyloidosis of heart, dentatorubral pallidoluysian atrophy, haemodialysis-associated amyloidosis, hereditary cerebral amyloid angiopathy, Gaucher's disease, medullary carcinoma of thyroid, hereditary cerebral amyloid angiopathy, cystic fibrosis, Marfan syndrome, fragile X syndrome, fragile XE syndrome, Finnish type familial amyloidosis, Alexander disease, light chain amyloidosis, Machado-Joseph disease, hereditary systemic amyloidosis, myotonic dystrophy, aquaporin-vasopressin-1, cancer, prion diseases, retinitis pigmentosa protein, secondary systemic amyloidosis, amyotrophic lateral sclerosis, frontotemporal dementia, and familial amyloid polyneuropathy.

BRIEF DESCRIPTION OF THE DRAWINGS

FIG. 2A is an amino acid sequence in which LxVP motif (SEQ ID NO: 10) exemplified by LAPP (SEQ ID NO: 12), SPP motif exemplified by SPPASPP (SEQ ID NO: 3), PxIxIT (SEQ ID NO: 9) exemplified by PSVVH (SEQ ID NO: 13), and TxxP (SEQ ID NO: 11) exemplified by TRRP (SEQ ID NO: 14) motifs are underlined, and residue numbers are indicated above the amino acid sequence. Below the amino acid sequence is an illustration of NMR results showing the location of secondary structure relevant to each binding motif. Secondary structures of the RCAN1:calcineurin complex include helix1 and helix2 shown as gray helices, and flex1 and flex2 shown as dashed lines. NMR data show that flex1 and flex2 remained flexible within the RCAN1:calcineurin complex.

FIG. 2B is a drawing of the amino acid positions of the amino acid sequences of RCAN1 constructs used in the Examples.

FIGS. 3A, 3B, and 3C are graphs of NMR characterization of RCAN1$^{89-197}$ (SEQ ID NO: 2).

FIG. 3A is a graph of the 2D $^1$H-$^{15}$N heteronuclear single quantum coherence (HSQC) spectrum of RCAN1$^{89-197}$ (SEQ ID NO: 2).

FIG. 3B is a graph of the chemical shift analysis showing the preferred secondary structure of RCAN1$^{89-197}$ (SEQ ID NO: 2).

FIG. 3C is a graph of the heteronuclear Overhauser effect ($^{15}$N-hetNOE) spectroscopy results.

FIGS. 4A and 4B are a graph and photographs of characterizations of the complex of RCAN1$^{128-164}$ (SEQ ID NO: 7) and calcineurin.

FIG. 4A is a graph of isothermal titration calorimetry (ITC) results showing that RCAN1$^{128-164}$ (SEQ ID NO: 7) binds to both calcineurin and CNA$_{cat}$ with an affinity, $K_d$, of about 280 nM. The $K_d$ of binding isotherm of RCAN1$^{128-164}$ (SEQ ID NO: 7) with calcineurin is 176 nM.

FIG. 4B is a photograph of size exclusion chromatography (SEC) profile of the complex of RCAN1$^{128-164}$ (SEQ ID NO: 7) and CNA$_{cat}$. Arrows indicate crystals suitable for optimization grown in potassium phosphate dibasic, 20% PEG3350 at pH 9.2.

FIGS. 5A-5B are drawings of PSP catalytic domains. PP1, PP2A, and calcineurin have a highly conserved catalytic domain (light grey).

FIG. 5A is a drawing of PP1 interacting with one of about 200 distinct, variable, and exchangeable regulatory proteins (dark grey), which function as inhibitory and targeting proteins. A few PP1 substrates bind directly to PP1, and the remaining substrates bind to other domains that are part of the PP1 regulatory proteins to enhance dephosphorylation. Alternatively, substrates are dephosphorylated because PP1 is localized in proximity to the substrate via its targeting proteins.

FIG. 5B is a drawing of PP2A catalytic domain with the variable and exchangeable regulatory subunit (B) and the invariant subunit (A). The catalytic domain PP2Ac interacts with an invariant A and about 25 regulatory B subunits to achieve substrate specificity in a manner similar to that of PP1. Substrates bind directly to PP2A or to domains in the regulatory subunits.

FIG. 5C is a drawing of calcineurin with subunits CaNB and CaNA. Calcineurin is regulated by calcium, which is required for activation. Calcineurin binds directly to substrates via protein interaction motifs that are also used by regulatory proteins because most regulatory proteins are also substrates. Most substrates bind directly to calcineurin.

FIGS. 6A-6B are models of mechanisms of inhibiting calcineurin by blocking substrate binding.

FIG. 6A is a model of a surface representation of calcineurin (light/dark grey) bound to A238L, a potent protein inhibitor of calcineurin from the African Swine Fever Virus. A238L inhibits calcineurin activity by binding to calcineurin substrate recognition grooves to block calcineurin from binding and dephosphorylating substrates. A238L binds calcineurin via both a PxIxIT (SEQ ID NO: 9) sequence (middle panel) and an LxVP (SEQ ID NO: 10) sequence. The deep groove in calcineurin engaged by the 'L' of the LxVP (SEQ ID NO: 10) motif (Leu229 in A238L) is indicated by a star.

FIG. 6B is a model of a surface representation of calcineurin (light and dark grey) bound to FK506 and CSA. The immunosuppressant drugs FK506 and Cyclosporin A (CSA) bind directly to the calcineurin LxVP (SEQ ID NO: 10) docking groove. A close-up view of FK506 in the calcineurin LxVP (SEQ ID NO: 10) binding groove, and an overlay with A238L are shown. The deep groove in calcineurin engaged by the 'L' of the LxVP (SEQ ID NO: 10) motif is indicated by a star and is fully engaged by FK506. Close-up views of CSA in the calcineurin LxVP (SEQ ID NO: 10) binding groove (left) and an overlay with A238L are shown.

FIGS. 7A-7B are models of PP1 regulatory protein docking grooves and a table listing the source regulatory subunit for a selection of motifs.

FIG. 7A is a model of a surface representation of PP1 with regulatory protein docking grooves labeled as RVxF (SEQ ID NO: 15), ΦΦ, Arg, SILK, MyPhoNE, NIPP1-helix, and Spino-helix. The Inhibitor-2 helix over the active site that directly inhibits PP1 activity is not shown.

FIG. 7B is a table that lists the PP1 regulators (189) that contain various motifs.

FIG. 8A is a model of the REG1:PP1 and REG2:PP1 holoenzymes. REG1 represents a PP1 regulatory protein that contains an RVxF-ΦΦ-Arg motif (RVxF is SEQ ID NO: 15), such as PNUTS. The holoenzyme is preferentially populated compared to the REG2:PP1 holoenzyme because the affinity of REG1 for PP1 is much higher than REG2 for PP1. REG2 is a PP1 regulatory protein with only an RVxF (SEQ ID NO: 15) motif.

FIG. 8B is a model of a mechanism of a drug that inhibits REG1. A drug that targets only the ΦΦ-Arg binding grooves will selectively displace the motifs in REG1 that bind at these sites, thereby reducing the affinity of REG1 for PP1 and, consequently, increasing the likelihood of forming REG2:PP1 holoenzymes. In this way, dephosphorylation of REG1:PP1 substrates will decrease while REG2:PP1 holoenzymes will increase.

DETAILED DESCRIPTION

Figure 1:
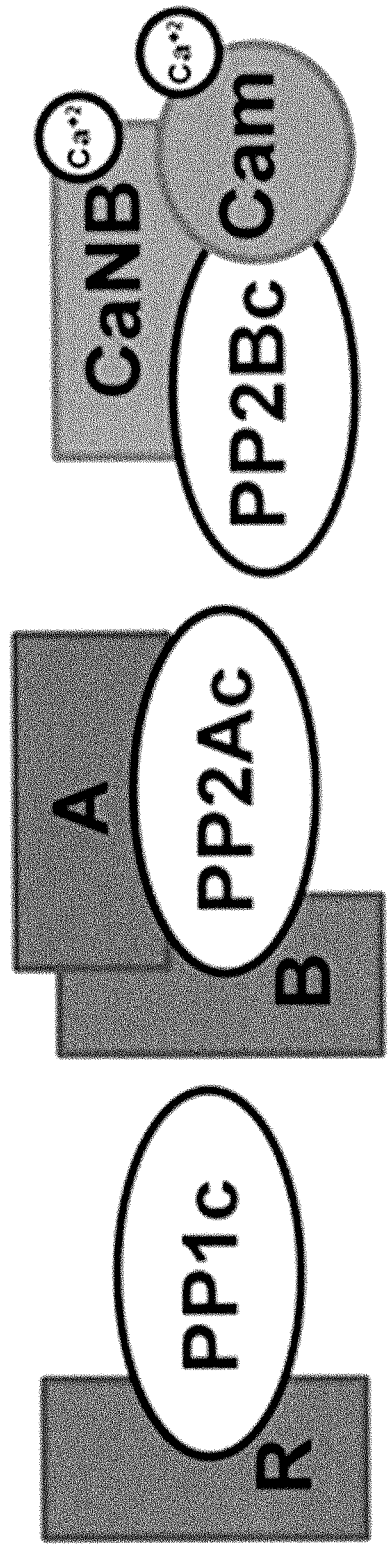
FIG. 1 is a drawing of functional components of a ser/thr protein phosphatase. The structures labeled PP1c, PP2Ac, and PP2Bc indicate core catalytic domains each weighing about 38 kDa. PP1 regulatory subunits are labeled R, and PP2A regulatory subunits are labeled A (constant) and B (variable).

Phosphorylation is a post-translational modification that controls many essential signaling cascades in neurons. See, Olsen et al., *Sci Signal,* 3(104): ra3 (2010). If neuronal signaling goes awry, the results cause disease, such as Alzheimer's disease and Down syndrome. It is important in treating disease to decipher the regulatory structural "language" that regulates PSPs, especially PP1 and calcineurin, and to predict how the amino acid sequence of more than 200 PP1 targeting proteins affects PP1 specificity from the amino acid sequence alone.

The Examples herein analyze protein ser/thr phosphatases (PSPs) calcineurin and PP1 to engineer molecules that regulate inhibitors of these proteins, such as RCAN1. See, Peti et al., *FEBS J* 280, 596-611 (2013); Braithwaite et al., *Prog Mol Biol Transl Sci* 106, 343-79 (2012). Rather than target active sites, these Examples have demonstrated that targeting PSP/PTP protein (substrate/regulatory) interaction sites, which are distal from the active sites, are highly viable and suitable drugs targets. This is especially true for calcineurin for which the immunosuppressant drugs FK506 and Cyclosporin A were demonstrated to bind and block one of the key calcineurin substrate interaction sites, the LxVP site (SEQ ID NO: 10). They function by potently inhibiting the activity of calcineurin by inhibiting substrates, especially the NFATs, from binding and, as a consequence, being dephosphorylated by calcineurin. See, FIG. 6; Grigoriu et al., *PLoS biology,* 11, e1001492 (2013); Rodriguez et al., *Mol Cell,* 33: 616-626 (2009).

The second characterized substrate recognition site in calcineurin is the PxIxIT (SEQ ID NO: 9) site, which binds PxIxIT (SEQ ID NO: 9) sequences in calcineurin regulators and substrates. See, Aramburu et al., *Mol Cell,* 1: 627-637 (1998); Li et al., *J Mol Biol,* 369: 1296-1306 (2007). However, the primary problem with targeting the PxIxIT (SEQ ID NO: 9) and LxVP (SEQ ID NO: 10) sites is that most calcineurin substrates, as well as regulatory and targeting proteins such as AKAPs contain a PxIxIT (SEQ ID NO: 9) or an LxVP (SEQ ID NO: 10) site. See, Li et al., *Nat Struct Mol Biol,* 19: 337-345 (2012). This likely explains the severe side effects of CSA and FK-506. While the targeted substrates, the NFATs, cannot be dephosphorylated and are result in the limited immune response that is critical for organ transplantations, other substrates with LxVP (SEQ ID NO: 10) sites will also be unable to bind and be dephosphorylated by calcineurin.

For calcineurin, the identification of additional protein interactions sites that are used by very few substrates and/or targeting proteins ought to be seen as the key step for the development novel calcineurin therapeutics, e.g. against neurological diseases. This is because novel drugs that target these sites will only disrupt the interaction of calcineurin with a very small number of targeting and/or substrates. Once identified, these sites will provide a powerful avenue for highly specific modulation of calcineurin activity. Additional Examples show that this approach, targeting substrate and/or regulatory protein interaction sites, holds incredible promise for PP1-related diseases. Finally, domains outside PTP catalytic domains have also recently been demonstrated to directly alter PTP activity.

Collectively, these insights offer transformative perspectives for the therapeutic targeting of PSPs by interfering with the binding of PIPs or substrates and PTPs by targeting allosteric sites outside their catalytic domains.

Results yield compositions that modulate calcineurin activity and methods to detect the similarities and differences between PSP and kinase substrate recognition. Ibid. RCAN1 is a trisomy 21 protein, viz. encoded on chromosome 21 and overexpressed in subjects with Down syndrome, leading to dysregulation of NFAT signaling and hyper-phosphorylation of tau resulting in Down syndrome and Alzheimer's disease. Ibid. Understanding how PP1 regulates translation initiation will identify routes for treating protein misfolding diseases such as Alzheimer's disease, Down syndrome, Parkinson's disease, amyotrophic lateral sclerosis, Huntington's disease, spongiform encephalopathies, familial amyloidotic polyneuropathy, type II diabetes, spinocerebral ataxia type 6, familial British dementia, Fabry's disease, spinobulbular muscular atrophy, ataxia, Wilson disease, atrial amyloidosis of heart, dentatorubral pallidoluysian atrophy, haemodialysis-associated amyloidosis, hereditary cerebral amyloid angiopathy, Gaucher's disease, medullary carcinoma of thyroid, hereditary cerebral amyloid angiopathy, cystic fibrosis, Marfan syndrome, fragile X syndrome, fragile XE syndrome, Finnish type familial amyloidosis, Alexander disease, light chain amyloidosis, Machado-Joseph disease, hereditary systemic amyloidosis, myotonic dystrophy, aquaporin-vasopressin-1, cancer, prion diseases, retinitis pigmentosa protein, secondary systemic amyloidosis, amyotrophic lateral sclerosis, frontotemporal dementia, and familial amyloid polyneuropathy.

The structural and functional characterizations herein provide a detailed understanding of calcineurin and PP1 activity and regulation in the brain and engineering of a therapeutic composition that selectively modulates these signaling cascades for medical benefit.

Once it has been activated by $Ca^+$ ions, calcineurin dephosphorylates NFATs resulting in translocation of the NFATs to the nucleus, and initiation of NFAT-regulated gene transcription. Perturbation of this signaling cascade results in disease. One cause of signaling interference is RCAN1 which is an inhibitor of calcineurin. Binding of RCAN1 to calcineurin at motifs that interact with calcineurin is speculated to regulate calcineurin activity. In one embodiment, the motif for interaction with calcineurin is contained within $RCAN1^{1-197}$ (SEQ ID NO: 1), the amino acid sequence of $RCAN1^{1-197}$ is SEQ ID NO: 1-MEEVDLQDLPSATIA-CHLDPRVFVD GLCRAKFESLFRTYDKDITFQYFKS-FKRVRINFSNPFSAADARLQLHKTEFLGKEMKLYF AQTLHIGSSHLAPPNPDKQFLISPPASPPVGWKQVE-DATPVINYDLLYAISKLGPGEKYEL HAATDTTPSV-VVHVCESDQEKEEEEEMERMRRPKPKIIQTRRPEYT-PIHLS.

Greater than about 650 PP1 regulators are predicted to be naturally occurring in vivo, and about 75 holoenzymes are predicted to be naturally occurring for PP2A. Regulatory non-substrate proteins use multiple mechanisms to modulate phosphatase activity. Inhibitory proteins confer specificity directly by binding and blocking the PSP active site. Targeting/scaffolding proteins confer specificity both directly and indirectly by either modulating PSP specificity towards substrates or by localizing them to distinct regions of the cell. See, Bollen, *Trends Biochem Sci* 26, 426-31 (2001); Cohen, *J Cell Sci* 115, 241-56 (2002). These regulatory non-substrate proteins use signaling via other mechanisms also, such as phosphorylation of targeting proteins or regulation by second messengers such as $Ca^{2+}$, which is necessary for activation of calcineurin to modulate phosphatase activity.

PP1 and calcineurin are metal dependent enzymes. The catalytic site of these PSPs is at the intersection of three substrate binding regions: the hydrophobic, the acidic, and the C-terminal grooves. Calcineurin regulation depends on calmodulin binding at the calcineurin calmodulin binding domain in response to increases in $Ca^{2+}$ levels for activation. See, Roy et al, *Sci Signal* 2, re9 (2009); Li et al., *Trends Cell Biol* 21, 91-103 (2011). Calmodulin binding disrupts the interaction of the calcineurin auto-inhibitory domain (AID) with the calcineurin catalytic core.

Regulatory proteins bind to PP1 via multiple PP1-binding motifs, with the primary PP1-binding motif being the RVxF motif (SEQ ID NO: 15). See, Meiselbach et al., *Chem Biol* 13, 49-59 (2006); Hendrickx et al., *Chem Biol* 16, 365-71 (2009); and Peti et al., *FEBS J* (2012). Additional docking sites, such as the SILK and MYPHONE motifs, also play roles in the regulation of PP1 substrate specificity. See, Hendrickx et al., *Chem Biol* 16, 365-71 (2009); Hurley et al., *J Biol Chem* 282, 28874-83 (2007); Marsh et al., *Structure* 18, 1094-103 (2010); Ragusa et al., *Nat Struct Mol Biol* 17, 459-64 (2010); Terrak et al., *Nature* 429, 780-4 (2004). Furthermore, structural characterization of PP1 holoenzymes have identified key new binding motifs, including the ΦΦ- and the Arg-motifs. See, O'Connell et al., *Structure* 20, 1746-56 (2012); Choy et al., *Proc Natl Acad Sci USA* 111, 4097-102 (2014). The number of PP1 docking sites demonstrates that regulatory proteins use a combinatorial approach to create PP1 holoenzymes.

Most naturally-derived inhibitors show minimal differences in potency against PP1, PP2A, and calcineurin. Kelker et al., *J Mol Biol*, 385: 11-21 (2009); Gehringer, *FEBS Lett*, 557: 1-8 (2004). Thus alternative routes for creating PP1 specific drugs must be pursued.

One approach is to target the PP1 regulatory proteins. Although the specificity of the PP1 catalytic domains is low, PP1 dephosphorylates its substrates with high specificity. To achieve this, PP1 interacts with more than 100 distinct regulatory subunits; namely, inhibitory proteins that potently inhibit phosphatase activity by binding and blocking the active site, and targeting proteins, proteins that localize PP1 to distinct regions of the cell while also directly modulating PP1-substrate interactions. See, FIG. 5 and FIG. 7; Bollen et al., *Trends Biochem Sci*, 35: 450-458 (2010); Nairn et al., *Neuropharmacology*, 47 Suppl 1, 14-23 (2004); Hurley, *J Biol Chem*, 282: 28874-28883 (2007); Dancheck et al., *Biochemistry*, 47: 12346-12356 (2008); Dancheck et al., *Biochemistry*, 50 (2011) 1238-1246; Marsh et al., *Structure*, 18: 1094-1103 (2010). Many PP1 targeting subunits, such as nuclear inhibitor of protein phosphatase type 1 (NIPP1), enhance the binding of specific substrates. See, O'Connell et al., *Structure*, 20: 1746-1756 (2012). For example, the forkhead-associated (FHA) domain of NIPP1 enhances the PP1-mediated dephosphorylation of substrates: cell division cycle 5-like (CDC5L) and SIT4-associating protein (SAP155). See, O'Connell et al., *Structure*, 20: 1746-1756 (2012); Minnebo et al., *Nucleic Acids Res*, 41: 842-854

(2013). However, others, such as spinophilin and PP1 nuclear targeting subunit (PNUTS), have been shown to bind PP1 substrate recognition sites, thereby inhibiting the dephosphorylation of a subset of substrates. See, Choy et al., *Proc Natl Acad Sci USA*, 111: 4097-4102 (2014); Ragusa et al., *FEBS Lett*, 585: 36-40 (2011); Ragusa et al., *Nat Struct Mol Biol*, 17: 459-464 (2010). Thus, they function identically to CSA and FK-506 with calcineurin; i.e., they inhibit substrates from binding the PSP and thereby selectively inhibit their dephosphorylation. See, Ragusa et al., *Nat Struct Mol Biol*, 17: 459-464 (2010).

Figures 8A, 8B:
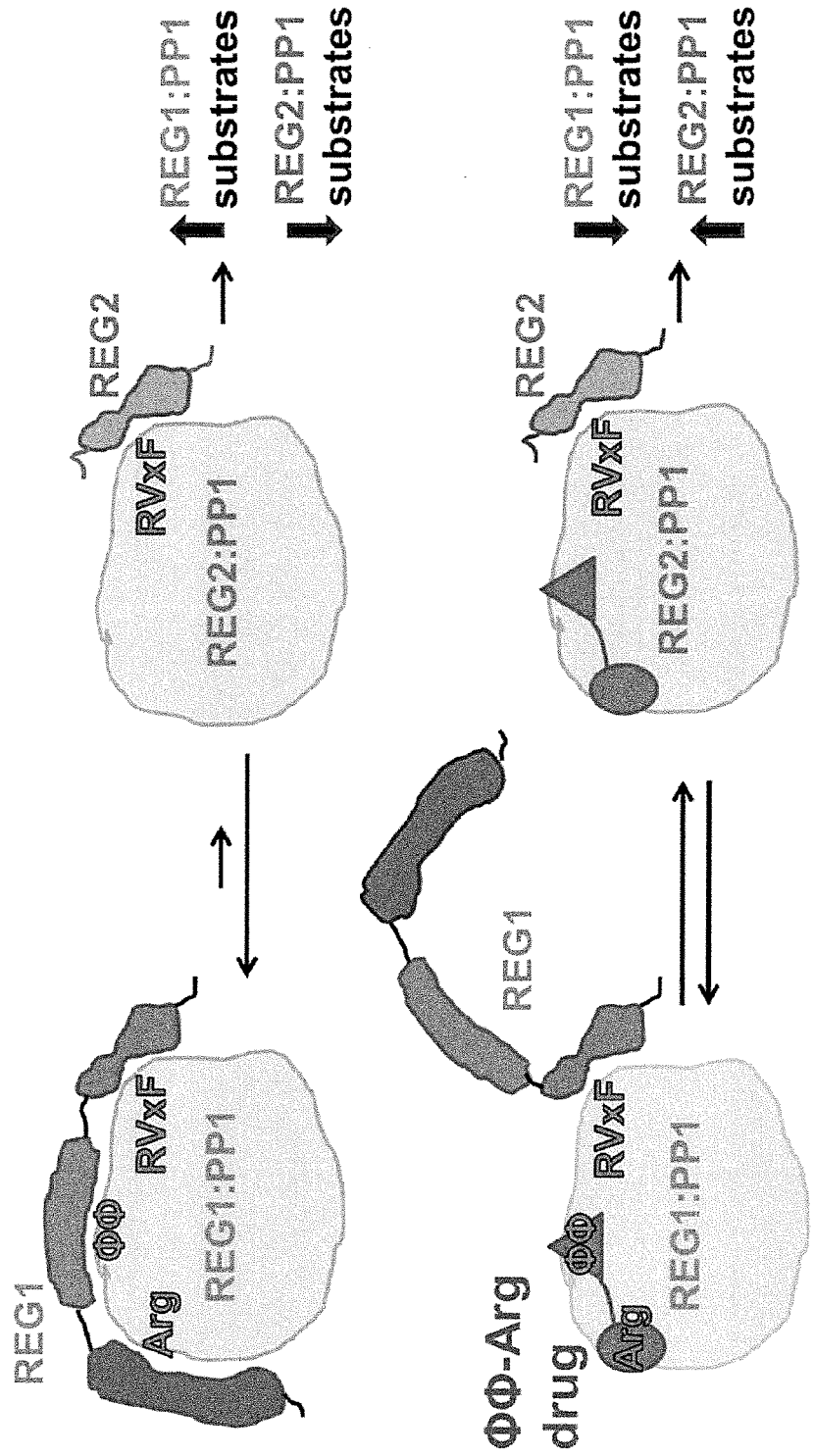
FIGS. 8A and 8B are models of mechanisms for developing drugs that inhibit only a subset of PP1 substrates. Toxins that bind and block the PP1 active site are lethal. Thus, any potential drugs that target PP1 must interact outside the PP1 active site. One approach is to target the PP1 regulatory protein docking grooves.
Figure 9:
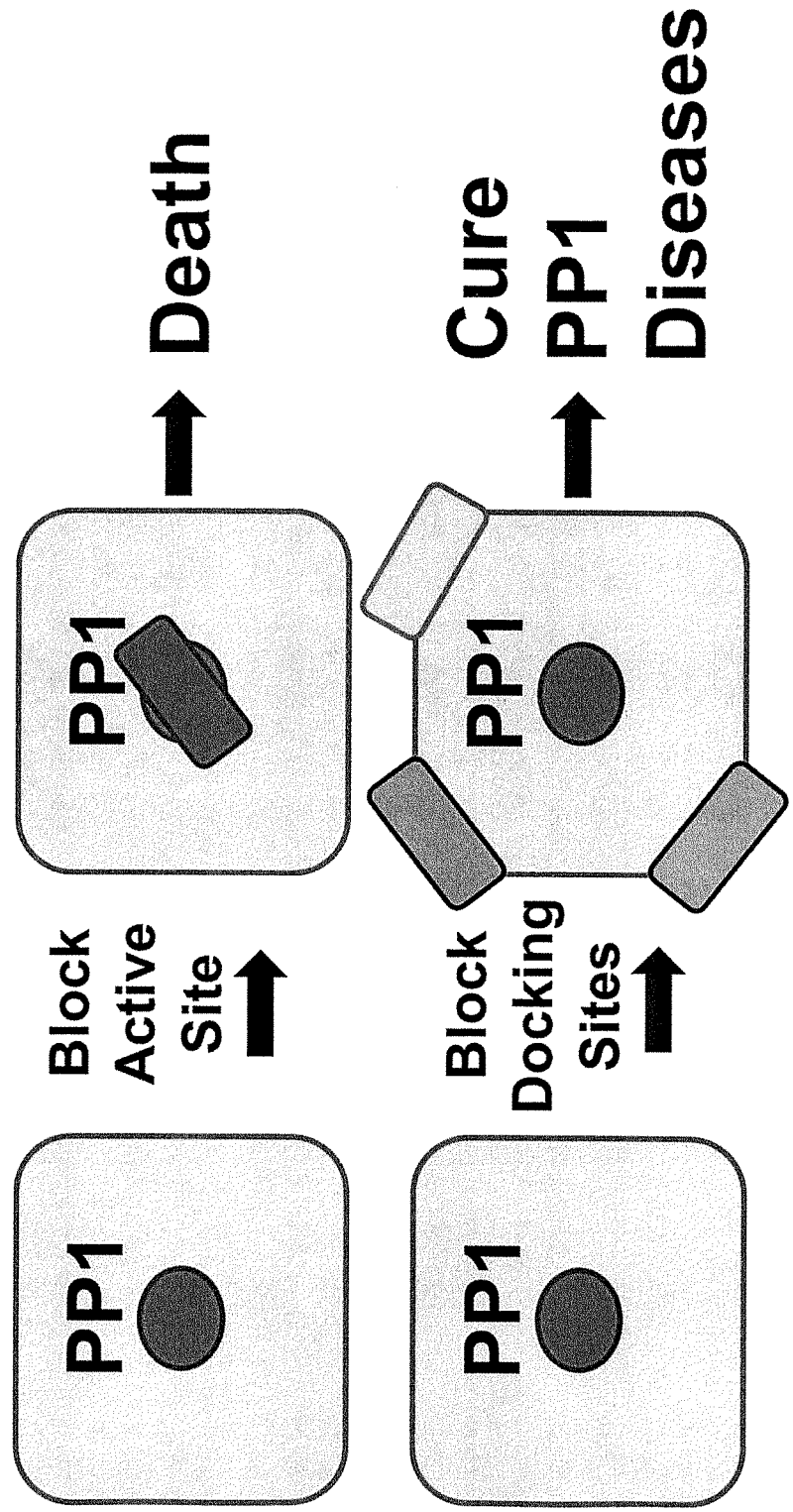
FIG. 9 is a drawing showing results of each of the two primary approaches to developing drugs for treatment of PP1-related diseases.

Therefore, one promising approach for developing PP1 specific drugs is to identify protein interaction sites that are specific for only a limited number of substrates and/or regulatory proteins. See, FIG. 7 and FIG. 8. This strategy provides a powerful and specific way to selectively modulate PP1 activity against a small subset of substrates and, in turn, target distinct signaling cascades. However, this strategy will also only be successful if the PP1 regulatory code is fully understood. See, Bollen et al., *Trends Biochem Sci*, 26: 426-431 (2001); Bollen et al., *Trends Biochem Sci*, 35: 450-458 (2010). In recent years, much progress has been made in elucidating the PP1 regulatory code. See, FIG. 7 and FIG. 8; Choy et al., *Proc Natl Acad Sci USA*, 111: 4097-4102 (2014). This was mainly driven by the structural assessment of new, additional PP1 holoenzymes, which has allowed for novel primary sequence motifs to be identified that either are necessary for binding PP1 and/or for changing its substrate specificity.

In Chatterjee et al., *Angewandte Chemie*, 51: 10054-10059 (2012); Chatterjee et al., *Current opinion in chemical biology*, 17: 361-368 (2013); Reither et al., *Chem Biol*, 20: 1179-1186 (2013), the authors developed a peptide based on the primary sequence of the PP1 regulator NIPP1 that includes the PP1 RVxF (SEQ ID NO: 15) and ΦΦ motifs, the two most prevalent PP1 binding motifs in all PP1 regulatory proteins. See also, Choy et al., *Proc Natl Acad Sci USA*, 111: 4097-4102 (2014). These studies showed that the peptide binds to PP1 and displaces many weaker binding targeting and inhibitory proteins in vitro and in vivo, abolishing the tight specificity of PP1 (by disrupting its interaction with targeting proteins) and increasing its activity (by disrupting its interaction with inhibitory proteins). The peptide based drug increased the overall general dephosphorylation in cells, which is potentially useful in diseases associated with global increases of phosphorylation, such as certain cancers. However, because the increase in dephosphorylation is now unregulated, drugs that target these interaction sites will likely not provide useful therapeutics for specific diseases. To further enhance this approach, more unique sites that are share by only a very small number of PP1 regulatory proteins, similar as suggested before for calcineurin.

There is now data that suggest it may be possible to selectively target a single PP1-specific pathway. Salubrinal and Guanabenz are small molecule drugs that have recently been shown to specifically inhibit translation by blocking the activity of eIF2α phosphatases, specifically CReP:PP1 and GADD34:PP1. See, Boyce et al., *Science*, 307: 935-939 (2005); Saxena et al., *Nat Neurosci*, 12: 627-636 (2009); Fullwood et al., *Progress in molecular biology and translational science*, 106: 75-106 (2012); Tsaytler et al., *Science*, 332: 91-94 (2011); Harding et al., *Proc Natl Acad Sci USA*, 106: 1832-1837 (2009); Jousse et al., *J Cell Biol*, 163: 767-775 (2003); Brush et al., *Mol Cell Biol*, 23: 1292-1303 (2003); Connor et al., *Mol Cell Biol*, 21: 6841-6850 (2001); Kojima et al., *FASEB journal: official publication of the Federation of American Societies for Experimental Biology*, 17: 1573-1575 (2003); Mikami et al., *Biotechnology letters*, 32: 897-902 (2010); Novoa et al., *J Cell Biol*, 153: 1011-1022 (2001). Whether or not this is achieved by selectively disrupting the PP1-substrate (eIF2α) and/or the PP1-regulatory protein (CReP, GADD34) remains to be determined. Finally, small molecules are also designed to bind specifically to the motifs/domains on substrates that mediate PSP binding, especially if substrate recruitment requires additional domains form the regulatory proteins that are distinct from the phosphatase binding domains. This approach can be applied to PP1 as well as to PP2A. See, Khanna et al., *Cancer research*, 73: 6548-6553 (2013).

Furthermore, because PP1, PP2A and calcineurin are responsible for the majority of the ser/thr dephosphorylation reactions in humans, inhibiting their active sites is also expected to disrupt many biological processes.

Calcineurin substrates use PxIxIT (SEQ ID NO: 9) and LxVP (SEQ ID NO: 10) sites on calcineurin for binding and dephosphorylation. CNA binds CNB via an extended α-helix (helix α14), called the CNB-binding helix, which extends away from the globular catalytic core.

Nfatc2$^{-/-}$ and Nfatc4$^{-/-}$ (nuclear factor of activated T-cells) knockout mice have facial characteristics related to those observed in patients with Down syndrome, providing evidence that NFAT signaling plays a central role in this disease. See, Arron et al., *Nature* 441, 595-600 (2006). NFAT signaling is initiated by Ca$^+$. An influx of Ca$^+$ into the cell activates calcineurin, which then dephosphorylates cytosolic NFATs, causing translocation into the nucleus and initiation of NFAT-regulated gene transcription. Because signaling cascades rely on a delicate balance of input and output signals, the deficiency of NFAT2 and NFAT4 in the NFAT knockout mice results in disease.

A signaling imbalance leading to a 50% increase in expression of a small group of genes occurs in individuals with chromosomal trisomy, e.g. those with Down syndrome. In Down syndrome, the protein product of one of these genes, DSCR1 (Down syndrome candidate region 1) commonly referred to as RCAN1, was recently identified to be an inhibitor of calcineurin. See, Kingsbury et al., *Genes Dev* 14, 1595-604 (2000); Hilioti et al., *Biochem Biophys Res Commun* 311, 1089-93 (2003).

RCAN1, also known as Adapt78, MCIP1, RCN1, and calcipressin, is a member of a small family of proteins including of RCAN1, RCAN2, and RCAN3. See, Panigrahi et al., *Chem Biol* 16, 928-36 (2009). Each protein member of the family has a molecular weight of about 25 kDa and shares about 80% amino acid sequence identity with the calcineurin binding domain. See, Panigrahi et al., *Chem Biol* 16, 928-36 (2009); Martinez-Martinez et al., *Proc Natl Acad Sci USA* 106, 6117-22 (2009); and Mehta et al., *Mol Cell Biol* 29, 2777-93 (2009). The 1.5-fold increase of RCAN1 due to trisomy results in increased inhibition of calcineurin, which disrupts NFAT signaling resulting in disease. Mice with forebrain specific deletions of CNB, which is responsible for making calcineurin activation sensitive to Ca$^{2+}$, exhibit defects in learning and memory, both established symptoms of Down syndrome.

RCAN1 is also overexpressed in patients with Alzheimer's disease. In subjects with Alzheimer's disease, RCAN1 levels are about three-fold higher than in non-diseased individuals. Down syndrome and Alzheimer's disease are linked symptomatically, in that Down syndrome patients that reach middle age (i.e. 40s) suffer from early onset Alzheimer's disease. They are also linked biochemically since the neurofibrillary tangles that are the hallmark of Alzheimer's disease are composed of the hyper-phosphorylated version of the protein tau. Many ser/thr as well as tyr phosphatases are critical for maintaining the proper tau phosphorylation state. See, Braithwaite et al., *Prog Mol Biol Transl Sci* 106, 343-79 (2012).

Calcineurin is highly enriched in neuronal tissues and makes up about 1% of the total protein in brain. Further, calcineurin plays a critical role in the control of tau phosphorylation and thus Alzheimer's disease physiology. Excess inhibition of calcineurin due to increased levels of RCAN1 has physiological consequences. To regulate calcineurin activity endogenously, RCAN1 engages calcineurin outside the canonical PxIxIT (SEQ ID NO: 9) and LxVP (SEQ ID NO: 10) motifs and these additional sites play a key role in how RCAN1 directs calcineurin activity.

Pharmaceutical Compositions

In one aspect of the present invention, pharmaceutical compositions are provided, such that these compositions include a molecule that binds a protein inhibitor of calcineurin, so that a function of calcineurin is increased. In certain embodiments, these compositions optionally further include one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington Twenty-second Edition "The Science and Practice of Pharmacy, Pharmaceutical Press 2012 discloses various carriers used in formulating pharmaceutical compositions and techniques for the preparation thereof. Some examples of materials which serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants could also be present in the composition, according to the formulator.

The Examples herein use structural biology, biophysics, and biochemistry to elucidate molecular mechanisms of inhibition of calcineurin by RCAN1. These Examples contain non-limiting embodiments of therapeutic compositions to treat protein serine/threonine phosphotase-related diseases.

Example 1

Identification of a the RCAN1 Calcineurin-Binding Domain

Figures 2A, 2B:
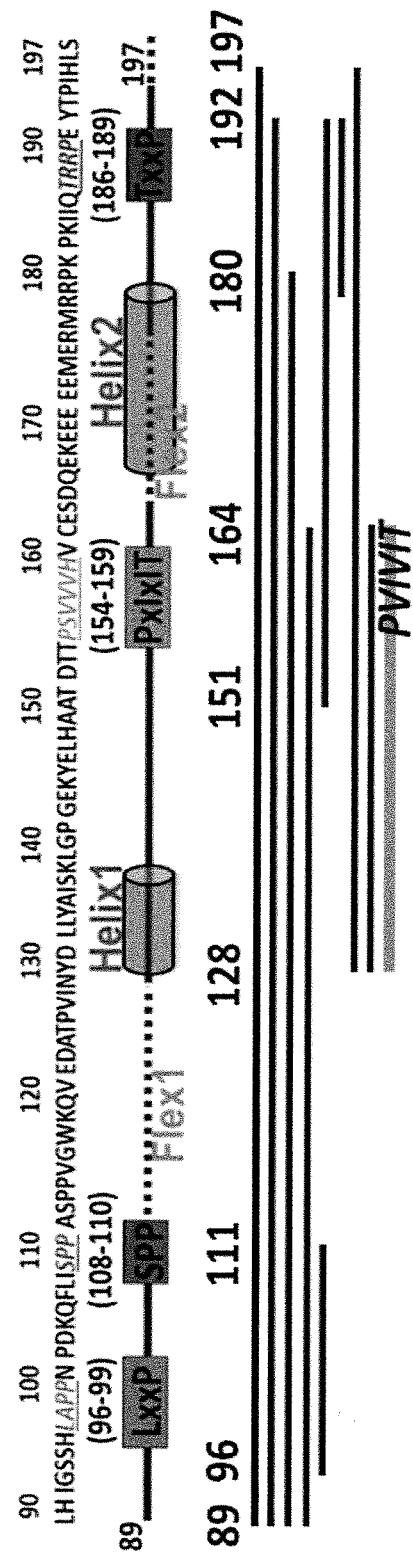
FIGS. 2A and 2B are drawings of an amino acid sequences and functional secondary structures in a calcineurin-binding domain of RCAN1.

RCAN1 has a structured RNA-binding domain (amino acid positions 1-88) at the N-terminus. ITC results show this domain does not interact directly with calcineurin. Instead, calcineurin interactions occur within RCAN1$^{89-197}$ (SEQ ID NO: 2), as shown in FIG. 2: $^{96}$LAPP$^{99}$ (SEQ ID NO: 12) is an example of the LxVP (SEQ ID NO: 10) motif and $^{154}$PSVVVH$^{159}$ (SEQ ID NO: 13) is an example of the PxIxIT (SEQ ID NO: 9) motif. Additional regions proposed to play a role in both calcineurin binding and regulation were observed to be: the $^{108}$SPPASPP$^{114}$ (SEQ ID NO: 3) motif which was hypothesized to act as a pseudo-substrate inhibitor, the $^{145}$ELH$^{147}$ (SEQ ID NO: 5) motif which was hypothesized to bind calcineurin, and the $^{186}$TxxP$^{189}$ (SEQ ID NO: 11) motif which was hypothesized to function in calcineurin metal biogenesis to interact at the calcineurin active site. See, Martinez-Martinez et al., *Proc Natl Acad Sci USA* 106, 6117-22 (2009) and FIG. 2.

Example 2

Identification of RCAN1 Residues Outside the Canonical Motifs that Interact Directly with Calcineurin Solution state NMR spectroscopy was used to fully characterize RCAN1 residues and motifs outside the canonical motifs that interact directly with calcineurin at a molecular level. RCAN1$^{89-197}$ (SEQ ID NO: 2) is an intrinsically disordered protein in solution. The amino acid sequence specific backbone assignment of RCAN1$^{89-197}$ (SEQ ID NO: 2) identified using chemical shift analysis two regions with preferred α-helical secondary structure elements: helix1—amino acid positions 130-138, about 40% populated; and helix2—amino acid positions 166-179, about 55% populated. See, FIG. 2A and FIG. 3B. These regions also have reduced fast timescale dynamics as determined using 15N-hetNOE techniques. See, FIG. 3C. The transiently structured regions correlate with the previously biochemically identified motifs.

Results of ITC show that calcineurin and RCAN1$^{89-197}$ (SEQ ID NO: 2) interacted strongly and had a $K_d$ of 10 nM. Based on this result, NMR was used to identify which residues of RCAN1$^{89-197}$ (SEQ ID NO: 2) bind directly to calcineurin. Only RCAN1$^{89-197}$ (SEQ ID NO: 2) was labeled with NMR active nuclei; calcineurin was unlabeled. The NMR data show that while most RCAN1$^{89-197}$ (SEQ ID NO: 2) residues interacted directly with calcineurin, residues in amino acid positions 114-127 (Flex1, C-terminal to the $^{108}$SPPASPP$^{114}$ (SEQ ID NO: 3) motif) and residues in amino acid positions 164-176 (Flex2) did not bind and instead remained flexible. See, FIG. 2. Flex2 was observed to partially overlaps with helix2.

NMR data was used to show that RCAN1$^{89-113}$, RCAN1$^{128-163}$, and RCAN1$^{177-189}$ (sequences within SEQ ID NO: 2) bound calcineurin at sites including the LxVP (SEQ ID NO: 10) and PxIxIT (SEQ ID NO: 9) motifs. To confirm that these motifs bound calcineurin, two RCAN1 mutants: HLAPP (SEQ ID NO: 16)→AAAAA (SEQ ID NO: 17) and PSVVVH (SEQ ID NO: 13)→ASAVAA (SEQ ID NO: 18), were synthesized and then analyzed by ITC. These variations resulted in a 2.5-fold and 220-fold decrease in $K_d$, respectively. RCAN1 PxIxIT (SEQ ID NO: 9) motif, and to a much lesser extent the LxVP (SEQ ID NO: 10) motif, were observed to contribute to calcineurin binding. NMR results show that residues outside the canonical LxVP (SEQ ID NO: 10) and PxIxIT (SEQ ID NO: 9) amino acid sequences interacted directly with calcineurin and thus constitute calcineurin interaction motifs that allow this holoenzyme to be selectively regulated.

Example 3

Determination of the Role of RCAN1$^{128-164}$ (SEQ ID NO: 7) in Calcineurin Binding To comprehensively characterize the role of RCAN1, especially residues RCAN1$^{128-164}$ (SEQ ID NO: 7) in calcineurin binding and regulation, ten different RCAN1 constructs (SEQ ID NOs: 2-11) were designed and synthesized. See, FIG. 2B. The constructs were engineered to contain the distinct interaction domains identified using NMR, ITC, and mutagenesis data. The constructs were expressed as GST- or MBP-fusion proteins and were purified using affinity chromatography, SEC chromatography, and heat purification. RCAN1 constructs are stable up to 95° C., as is typical for intrinsically disordered proteins. The constructs are highly soluble and are concentrated to greater than or equal to 1 mM concentration. As long as they are thoroughly protected from protease degradation, e.g. by autoclaved purification buffers and 1 M NaOH washes of all purification equipment/columns, the constructs were viable in storage for long periods of time at −80° C.

The following are exemplary amino acid sequences of the RCAN1 constructs synthesized herein.

SEQ ID NO: 2-LHIGSSHLAPPNPDKQFLISPPASP-PVGWKQVEDATPVINYDLL YAISKLGPGEKYEL-HAATDTTPSVVVHVCESDQEKEEEEEMERMRRPKP-KIIQTRRPEYT PIHLS, which is RCAN1$^{89-197}$.

SEQ ID NO: 3-SPPASPP, which is RCAN1$^{108-414}$.

SEQ ID NO: 4-DLLYAISKL, which is RCAN1$^{130-138}$.

SEQ ID NO: 5-ELH, which is RCAN1$^{145-147}$.

SEQ ID NO: 6-EKEEEEEMERMRRP, which is RCAN1$^{166-179}$.

SEQ ID NO: 7-NYDLLYAISKLGPGEKYELHAAT-DTTPSVVVHVCESD, which is RCAN1$^{128-164}$.

SEQ ID NO: 8-NYDLLYAISKLGPGEKYELHAATDTT, is RCAN1$^{128-153}$.

SEQ ID NO: 9-PxIxIT, SEQ ID NO: 10-LxVP, and SEQ ID NO: 11-TxxP, are amino acid sequences of the calcineurin binding domains of RCAN1 shown in the Examples herein. Each "x" represents a single amino acid residue.

Affinity of each RCAN1 construct for calcineurin was measured using ITC to determine the individual contribution of each motif to binding. It was observed that RCAN1$^{128-164}$ (SEQ ID NO: 7), which includes helix1, $^{145}$ELH$^{147}$ (SEQ ID NO: 5) motif, and PxIxIT (SEQ ID NO: 9) motif, is important for calcineurin binding. See, FIG. 2A. If either the PxIxIT (SEQ ID NO: 9) motif or helix1 were deleted, the binding affinity was observed to have decreased 220- and 30-fold, respectively.

These results show that helix1 constitutes a calcineurin interaction motif that has not previously been identified in any other calcineurin regulatory protein.

The CNB subunit was analyzed to determine whether the subunit influences binding by generating a construct of only the calcineurin catalytic domain, CNA$_{cat}$ containing residues 1-348, and identical to a previously characterized CNA construct. See, Takeuchi et al., Structure 15, 587-97 (2007). This construct was observed to show full activity against pNPP and to have an identical structure to the corresponding domain from the CNA/B complex. ITC results showed that RCAN1$^{128-164}$ (SEQ ID NO: 7) binds to both calcineurin and CNA$_{cat}$ with equal affinities at a $K_d$ of about 280 nM. See, FIG. 4A. Affinity between RCAN1$^{128-164}$ (SEQ ID NO: 7) and calcineurin increased about 2-fold to a $K_d$ of 150 nM by mutating PSVVVH (SEQ ID NO: 13) to PVIVIT (SEQ ID NO: 19). The $K_d$ between RCAN1$^{128-164}$ (SEQ ID NO: 7) and CNA$_{cat}$ was not altered in the presence of EDTA, indicating that binding is independent of metals that are bound to the calcineurin active site. A similar analysis is not possible with CNA/B.

Example 4

Determination of Molecular Mechanism of RCAN1$^{128-164}$ (SEQ ID NO: 7) Binding to Calcineurin to Identify a Potentially Regulatable RCAN1-Specific Interaction Groove on Calcineurin Data revealed that residues outside the canonical LxVP (SEQ ID NO: 10) and PxIxIT (SEQ ID NO: 9) sequences interacted directly with calcineurin, and which will allow this holoenzyme to be selectively regulated. As shown by ITC, the RCAN1 constructs formed highly stable complexes with calcineurin. The constructs and calcineurin co-eluted during SEC. Further crystallization analysis focused on the complex of RCAN1$^{128-164}$ (SEQ ID NO: 7) and calcineurin because RCAN1$^{128-464}$ (SEQ ID NO: 7) binds tightly to calcineurin, yet does not contain any flexible regions which inhibit crystallization.

RCAN1$^{128-164}$ (SEQ ID NO: 7) bound to CNA$_{cat}$ and calcineurin (CNA/B) with identical affinities as shown by ITC. Crystallization trials were performed with both constructs. The purification of the complex of RCAN1$^{128-164}$ (SEQ ID NO: 7) and calcineurin used essentially the same protocol as used for formation of the A238L:calcineurin complex in Grigoriu et al., PLoS Biol 11, e1001492 (2013), which is hereby incorporated by reference in its entirety. The complex of RCAN1$^{128-164}$ (SEQ ID NO: 7) and CNA$_{cat}$ was formed by purifying each protein separately, incubating the two proteins together in 2:1 ratio (RCAN1$^{128-164}$:CNA$_{cat}$). The complex was purified using SEC (Superdex 75). See, FIG. 4B. Both the RCAN1$^{128-164}$: calcineurin and RCAN1$^{128-164}$:CNA$_{cat}$ complexes were stable and were concentrated to 7 or 20 mg/ml, respectively. Small crystals (about 5 μm$^3$) of the RCAN1$^{128-164}$:CNA$_{cat}$ complex were obtained. Fine-screening, additive screening, and seeding were used to obtain crystals suitable for structure determination of RCAN1$^{128-164}$:calcineurin, RCAN1$^{128-164}$:CNA$_{cat}$, and additional RCAN1 constructs. See, FIG. 4B.

Example 5

Elucidating the Role of the Txxp (SEQ ID NO: 11) Motif in Calcineurin Binding and Regulation The N$^H$, N cross-peaks corresponding to RCAN1 TxxP (SEQ ID NO: 11) motif residues were not visible in the 2D [$^1$H,$^{15}$N] HSQC spectrum of the complex of RCAN1$^{89-197}$ (SEQ ID NO: 2) and calcineurin, indicating under these conditions either that: the TxxP (SEQ ID NO: 11) motif bound to calcineurin, or that the TxxP (SEQ ID NO: 11)

motif was in the proximity of the calcineurin active site though not necessarily bound and the loss of signal was due to the paramagnetic effect of the active site metals ($Zn^{2+}$/$Fe^{3+}$). Previous characterizations show that the TxxP (SEQ ID NO: 11) amino acid sequence inhibited pNPP dephosphorylation, and thus likely bound at the active site. See, Chan et al., *Proc Natl Acad Sci USA* 102, 13075-80 (2005).

Results of ITC performed with a construct including the $^{186}$TxxP$^{189}$ (SEQ ID NO: 11) motif showed a distinct, bimodal isotherm. Bimodal isotherms are typically indicative of multiple ligands binding to single protein (i.e. 2:1 stoichiometry). However, the SEC and dynamic light scattering (DLS) data showed that the RCAN1:calcineurin complex has 1:1 stoichiometry (heterodimer). See, Peti et al., *Bioorganic and Medicinal Chemistry*, 23: 2781-2785 (2015), which is hereby incorporated by reference in its entirety. A bimodal isotherm arising from a 1:1 complex is rare. In such a case, binding at the first site must overcome a high activation energy barrier to induce a major change in the macromolecule to expose the second binding site. The change in molecular structure confirms the role of the TxxP (SEQ ID NO: 11) motif in calcineurin-metal biogenesis.

To determine how the TxxP (SEQ ID NO: 11) motif binds and engages calcineurin, the residues within and surrounding the TxxP (SEQ ID NO: 11) motif were mutated (i.e. K182A/E, Q185A, E190R/A, Y191A) and ITC was used to quantify which residues are most critical for calcineurin binding. ITC was used to determine whether the TxxP (SEQ ID NO: 11) motif binds only the CNA catalytic domain, or also requires CNB for binding using RCAN1$^{128-197}$, without requiring the LxVP (SEQ ID NO: 10) motif. Calcineurin active site residues were mutated as follows: R122A/D, H151A, D118A, R254A/D; and the change in affinity was quantified. ITC under acidic (pH=5) conditions showed that the active site metals were displaced, as observed in characterization of A238L:calcineurin crystal structure shown in Grigoriu et al., *PLoS Biol* 11, e1001492 (2013), which is incorporated by reference in its entirety herein. The peptide consisting of RCAN1$^{178-192}$ (within SEQ ID NO: 2) that includes the TxxP (SEQ ID NO: 11) site was observed not to bind to calcineurin. However, TxxP (SEQ ID NO: 11) was bound to calcineurin at $K_d$=15 µM as measured by ITC, when titrated into the pre-formed complex of RCAN1$^{128-164}$ (SEQ ID NO: 7) and calcineurin. Furthermore, RCAN1$^{128-192}$ (within SEQ ID NO: 2), which includes RCAN1$^{128-164}$ (SEQ ID NO: 7) and the TXXP (SEQ ID NO: 11) site, binds with similar strength as RCAN1$^{128-164}$ (SEQ ID NO: 7) having a $K_d$ of about 300 nM as measured by ITC and with a bimodal isotherm. These data demonstrate the importance of residues RCAN1$^{128-164}$ (SEQ ID NO: 7) for calcineurin binding.

Example 6

Translation of Structural Results into Functional Chemical Entities Using In Vivo Assays The biochemical and structural characterizations above were further analyzed using in vivo substrate dephosphorylation and functional NFAT assays. Dephosphorylation of validated calcineurin substrates including phospho-T34-inhibitor-1, RII, and NMDA receptor NR2B were examined in transfected cell lines. See, Katz et al., *Chem Soc Rev* 40, 2131-45 (2011); Francis et al., *Nat Chem Biol* 7, 916-24 (2011); and Matus et al., *Curr Opin Cell Biol* 23, 239-52 (2011). The effects of RCAN-derived peptides on phosphorylation of tau in neurons in culture were analyzed using similar approaches to those used in Boyce et al., *Science* 307, 935-9 (2005). Peptides were designed based on prior structural characterizations using available stable or transfected cell lines or neurons in primary culture. These peptides were hypothesized to specifically disrupt RCAN1 mediated calcineurin signaling. A local regulatory imbalance of NFAT function is known to be the underlying cause of Down syndrome. See, Arron et al., *Nature* 441, 595-600 (2006); Fuentes et al., *Hum Mol Genet* 9, 1681-90 (2000).

To determine whether RCAN1$^{128-164}$ (SEQ ID NO: 7) peptide is a selective inhibition reagent in NFAT reported assays, the results were compared with levels of FK506 and CSA inhibition. An RCAN1$^{128-153}$ (SEQ ID NO: 8) peptide that did not include the RCAN1 PxIxIT (SEQ ID NO: 9) motif was synthesized, and the NFAT assays described herein were performed. RCAN1$^{128-153}$ (SEQ ID NO: 8) was observed to be highly selective, and to selectively disrupt the RCAN1:calcineurin complex, but to have no other (or minimal) physiological consequences. Poly-R amino acid sequences are added to the N-terminus of the peptide to facilitate cell membrane translocation, if needed. The peptide as well as the structure of the complex of RCAN1$^{128-164}$ (SEQ ID NO: 7) and calcineurin were optimized using SPOT technology, if effective only at high peptide concentrations due to weaker interaction with calcineurin, as a guide to develop a Down syndrome biologic. See, Fullwood et al., *Prog Mol Biol Transl Sci* 106, 75-106 (2012).

Example 7

Additional Embodiments

The data herein from protein production, NMR, ITC, and crystallization techniques demonstrates the utility of the embodiments shown herein. NMR spectroscopy is used to gain further molecular insights into the interaction of RCAN1$^{128-164}$ (SEQ ID NO: 7) and CNA. Previous results show the feasibility of using NMR spectroscopy to characterize CNA. See, Takeuchi et al., *Structure* 15, 587-97 (2007). In NMR spectroscopy, the complex concentrated up to about 0.5 mM is stable for days, and the data herein proves that NMR spectroscopy is successfully used with large complexes, such as CNA. See, Dancheck et al., *Biochemistry* 50, 1238-46 (2011); Rutkowski et al., *Trends Biochem Sci* 32, 469-76 (2007). These approaches determine which residues of RCAN1 and calcineurin interact, especially at the calcineurin interaction site described herein.

What is claimed is:

1. A method for treating a protein serine/threonine phosphatase-related disease, the method comprising the steps of:
   administering to the subject a composition that disrupts interaction between a protein inhibitor RCAN1 (SEQ ID NO:1) and a protein serine/threonine phosphatase calcineurin in the subject, wherein the protein inhibitor inhibits at least one function of the calcineurin protein serine/threonine phosphatase, wherein the composition comprises a peptide comprising an amino acid sequence selected from the group of SEQ ID nos: 3, 5, 7, 8, 13, and 14;
   increasing the function of the calcineurin protein serine/threonine phosphatase compared to the function prior to the administering and decreasing a symptom of the calcineurin protein serine/threonine phosphatase-related disease;
   thereby treating the subject for the disease wherein the disease is Down syndrome or type II diabetes.

2. The method according to claim 1, wherein the protein inhibitor is not a substrate for phosphatase function of the protein serine/threonine phosphatase.

3. The method according to claim 1, further comprising prior to administering, formulating the composition to include at least one portion of calmodulin and $Ca^{2+}$ ions, and the portion having affinity to bind the calcineurin thereby disengaging the calcineurin autoinhibitory domain to expose a catalytic site of the calcineurin and increasing the function of the calcineurin.

4. The method according to claim 1, wherein the composition comprises at least one of a targeting protein or a scaffolding protein.

5. A method of disrupting the interaction between calcineurin and an inhibitor, the method comprising:
   synthesizing a molecule comprising at least one amino acid sequence selected from the group consisting of: SEQ ID NOs 3, 5, 7, 8, 13, and 14 and
   disrupting by the molecule an interaction between calcineurin and a protein inhibitor.

* * * * *